US006593147B1

(12) United States Patent
Barbet et al.

(10) Patent No.: US 6,593,147 B1
(45) Date of Patent: Jul. 15, 2003

(54) NUCLEIC ACID VACCINES AGAINST RICKETTSIAL DISEASES AND METHODS OF USE

(75) Inventors: Anthony F. Barbet, Archer, FL (US); Michael V. Bowie, Gainesville, FL (US); Roman Reddy Ganta, Manhattan, KS (US); Michael J. Burridge, Gainesville, FL (US); Suman M. Mahan, Harare (ZW); Travis C. McGuire, Pullman, WA (US); Fred R. Rurangirwa, Pullman, WA (US); Annie L. Moreland, Trenton, FL (US); Bigboy H. Simbi, Harare (ZW); William M. Whitmire, Hamilton, MT (US); Arthur R. Alleman, Alachua, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 09/553,662

(22) Filed: Apr. 21, 2000

Related U.S. Application Data

(63) Continuation-in-part of application No. 09/337,827, filed on Jun. 22, 1999, now abandoned, which is a division of application No. 08/953,326, filed on Oct. 17, 1997, now Pat. No. 6,251,872, which is a continuation-in-part of application No. 08/733,230, filed on Oct. 17, 1996, now Pat. No. 6,025,338.
(60) Provisional application No. 60/130,725, filed on Apr. 22, 1999.

(51) Int. Cl.[7] ............................................. G01N 33/543
(52) U.S. Cl. ........................ 436/518; 436/501; 435/7.1
(58) Field of Search .................... 435/7.1, 7.9, 7.91, 435/7.92, 7.93, 7.94, 7.95; 436/501, 518; 530/300, 324, 325, 326, 327, 328, 329, 350, 820

(56) References Cited

U.S. PATENT DOCUMENTS

| 4,879,213 | A |   | 11/1989 | Fox et al. |
| 5,643,578 | A |   | 7/1997  | Robinson et al. |
| 5,783,441 | A |   | 7/1998  | Carl et al. |
| 6,392,023 | B1 | * | 5/2002  | Walker et al. |
| 6,403,780 | B1 | * | 6/2002  | Walker et al. |
| 6,458,942 | B1 | * | 10/2002 | Walker et al. |

FOREIGN PATENT DOCUMENTS

| WO | WO 9012030 |   | 10/1990 |
| WO | 9816554    |   | 4/1998  |
| WO | 99/13720   | * | 3/1999  |

OTHER PUBLICATIONS

Lazar, Eliane, Shinichi Watanable, Stephen Dalton, Michael B. Sporn (1988) "Transforming Growth Factor α:Mutation of Aspartic Acid 47 and Leucine 48 Results in Different Biological Activities" Molecular and Cellular Biology 8(3):1247–1252.
DuPlessis, J.L. (1970) "Immunity in Heartwater: I.A. Preliminary note On The Role Of Serum Antibodies" Onderstepoort J. Vet Res. 37(3):147–150.
Uilenberg, Gerrit (1983) "Heartwater (Cowdria ruminantium Infection): Current Status" Advances In Veterinary Science and Comparative Medicine 27:427–480.
Vishwanath, Suryanarayanan, Gregory A. McDonald, Nancy G. Watkins (1990) "A Recombinant *Rickettsia conorii* Vaccine Protects Guinea Pigs from Experimental Boutonneuse Fever and Rocky Mountain Spotted Fever" Infection and Immunity 58(3):646–653.
van Vilet, A., F. Jongejan, M. vanKleef, B. Zeijst van der (1994) "Molecular Cloning, Sequence Analysis, and Expression of the Gene Encoding the Immunodorminant 32–Kilodalton Protein of *Cowdria ruminanthium*" Infection and Immunity 62(4):1451–1456.
Ulmer, J.B. et al. (1993) "Heterologous Protection Against Influenza by Injection of DNA Encoding a Viral Protein" Science 259:1745–1749.
Schödel, M.–T. Agaudo, P.–H. Lambert (1994) "Introduction: Nucleic Acid Vaccines, WHO, Geneva, May 17–18, 1994" Vaccine 12(16): 1491–1492.
Sedegah, Martha, Richard Hedstrom, Peter Hobart, Stephen L. Hoffman (1994) "Protection against malaria by immunization with plasmid DNA encoding circumsporozoite protein" Proc. Natl. Acad. Sci. USA 91:9866–9870.
Cox, J.M. Graham, Tim J. Zamb, Lorne A. Babiuk (1993) "Bovine Herpesvirus: 1: Immune Responses in Mice and Cattle Injected with Plasmid DNA" Journal of Virology 67(9):5664–5667.
Burgess, Wilson H., Anne M. Shaheen, Mark Ravera, Michael Jaye, Patrick J. Donohue, Jeffrey A. Winkles (1990) "Possible Dissociation of the Heparin–binding and Mitogenic Activities of Heparin–binding (Acidic Fibroblast) Growth Factor–1 from Its Receptor–bdining Activities by Site–directed Mutagenesis of a Single Lysine Residue" Journal of Cell Biology 111:2129–2138.
Ulmer, Jeffrey B., John J. Donnelly, Margaret A.Liu (1996) "DNA Vaccines Promising: A New Approach to Inducing Protective Immunity" ASM News 62(9):476–479.
Sumner, John W., Kim G. Sims, Dana C. Jones, Burt E. Anderson (1995) "Protection of guinea–pigs from experimental Rocky Moutain spotted fever by immunization with baculovirus–expressed *Rickettsia rickettsii* rOmpA protein" Vaccine 13(1):29–35.
Oberle, Suzan M., Anthony F. Barbet (1993) "Derivation of the complete msp–4 gene sequence of Anaplasma marginale without cloning" Gene 136:291–294.

(List continued on next page.)

*Primary Examiner*—Patricia A. Duffy
(74) *Attorney, Agent, or Firm*—Saliwanchik, Lloyd & Saliwanchik

(57) ABSTRACT

Described are nucleic acid vaccines containing genes to protect animals or humans against rickettsial diseases. Also described are polypeptides and methods of using these polypeptides to detect antibodies to pathogens.

6 Claims, 8 Drawing Sheets

OTHER PUBLICATIONS

Reddy, G. Roman, C.R. Sulsona, R.H. Harrison, S.M. Mahan, M.J. Burridge, A.F. Barbet (1996) "Sequence Heterogeneity of the Major Antigenic Protein 1 Genes from *Cowdria ruminantium* Isolates from Different Geographical Areas" Clinical and Diagnostic Laboratory Immunology 3(4):417–422.

Mahan, S.M., T.C. McGuire, S.M. Semu, M.V. Bowie, F. Jongejan, F.R. Rurangirwa, A.F. Barbet (1994) "Molecular cloning of a gene encoding the immunogenic 21 kDa protein of *Cowdria ruminantium" Microbiology* 140:2135–2142.

McGuire, Travis C., Edward B. Stephens, Guy H. Palmer, Terry F. McElwain, Carol A. Lichtensteiger, Steve R. Lieb, Anthony F. Barbet (1994) "Recombinant vaccinia virus expression of *Anasplasma marginale* surface protein MSP–1A: effect of promoters, lead sequences and GPI anchor sequence on antibody response" *Vaccine* 12(5):465–471.

Rurangirwa, Fred R., David Stiller, Dorthy French, Guy H. Palmer (1999)"Restriction of major surface protein 2 (MSP2) variants during tick tranmission of the ehrlichia Anaplasma marginale" *Proceedings of the National Academy of Sciences of the United States of America* 96(6): (abstract) only.

Lewis, Jr., G.E., D.L. Huxsoll, M. Ristic, A.J. Johnson (1975) "Experimentally induced infection of dogs, cats, and nonhuman primates with Ehrlichia equi, etiologic agent of equine ehrlichiosis" *Am. J. Vet. Res.* 36(1) (abstract) only provided and abstract only considered.

Rameshi, Vemulapalli, Biswajit Biswas, Sukanta K. Dutta (1995) "Pathogenic, immunologic, and molecular differences between two Ehrlichia risticii strains" *Journal of Clinical Microbiology* 33(11):. (abstract) only provided and abstract only considered.

Breitschwerdt, Edward B., Barbara C. Hegarty, Susan I Hancock (1998) "Doxycycline hyclate treatment of experimental canine . . . Ehrlichia canis strains" *Antimicrobial Agentw and Chemotherapy* 42(2): (abstract only).

Dutta, Sukanta K. et al. (1998) "Association of deficiency ina ntibody response to vaccine and heterogeneity of Ehrlichia risticii strains with Potomac horse fever vaccine failure in horses" *Journal of Clinical Microbiology* 36(2): (abstract) only.

Rikishia et al Journal of Clinical Microbiology 32(9):2107–2112, 1994.*

Kelly et al. Research in Veterinary Science 56:170–174, 1994.*

Brouqui et al, Clinical and Diagnostic Laboratory Immunology 1(6):645–649, 1994.*

Bowie, Michael V. et al. (1999) "Potential Value of Major Antigenic Protein 2 for Serological Diagnosis of Heartwater and Related Ehrlichial Infections" Clinical and Diagnostic Laboratory Immunology 6(2):209–215.

Nyika, A. et al. (1999) "A DNA vaccine protects mice against the rickettsial agent *Cowdria ruminantium*" Parasite Immunology 20:111–119.

* cited by examiner

FIG. 1A

```
C.r.  ATGAATTGCAAGAAAATTTTA---------------TCACAAGTACACTAATATCATTAGTG
E.c.  ATGAATTACAAGAAAAAGTTTCA--------------TAACAGCG-ATTGATATCATTAATA
A.m.  ATGAATTACAGAGAGAATTGTTTACAGGGGCCTG-TCAGCAGCC-ACAGTCTGCGCCTGCT
      ******* **           **     * ** **  *

C.r.  TCATTTT---TACCTGGTGTGTCCTTTTCTGATGTAATACAGGAAGACAGCAACCCAGCAG
E.c.  TCCTTCTCTTACCTGGACTGGAGTATCATTTTCCGACCCAAGGCAGGTAGTGGTCA---TTAACG
A.m.  CCCTACTTGTTAGTGGGGCCGTAGTGCCATGTCCCATGAGTCACGAAGTGGCTTCTGAAG
      *  * *    * *   ***   *     *  *         *    *            *

C.r.  GCAGTGTTTACATTAGCGCAAAATACATGCCAACTGCATCACATTTTGGTAAAATGTCAA
E.c.  GTAATTCTACATCAGTGGAAAATACAACAGTTGGACTTCGCATTTTGGAGTATTCTCTG
A.m.  GGGGAGTAATGGGAGGTAGCTTTACGTGGGTGCGGCCT-ACAGCCCAGCATTTCCTTCT
      *         *   *   * *        *           *          *    *

C.r.  TCAAAGAAGATTCAAAAAATACTCAAACGTATTGGTCTAAAAAAAGATTGGGATGGCG
E.c.  CTAAGGAAGAAGAATACAACAGTTGGAGTGTTGGACTGAAGCAAAATTGGGACGGAA
A.m.  GTTACCTCGTTCGACATGCGTGAGTCAAGAGACCTCA---TACGTTAGAGGCTATG
       *    *         *        **    *   * ** * *  * **     *

C.r.  TTAAAACACCACCATCAGATTCTAGCAATACTAATTCTACACAATTTTACTGAAAAAGACTATT
E.c.  GCGCAATATC--CAACTCCTCCCCAAACGA------TGTATTCACTGTCTCAAATTATT
A.m.  ACAAGAGCATTGCAACGATTGCAACGATTGATGTGAGTGTGCCAGCAAACTTTCCAAATCTGCTACA
        *   *  **      *  *  *     *          *  *  *   *  * ** **

C.r.  CTTTCAGATATGAAAACAATCCGTTTTTAGGTTTCGCTGGAGCAATTGGGTACTCAATGA
E.c.  CATTTAAATATGAAAACAACCGTTTTAGGTTTTGCAGGAGCTATTGGTTACTACTCAATGG
A.m.  CTTTGCCTTCTCTAAAAACTTAATCACGTCTTTCGACGGCGCTCTTCGACGTCTTTCTGG
      * **         *   *     **  * **   * ** **      *   * ** **
```

```
C.r.  ATGGACCAAGAATAGAGTTCGAAGTATCCTATGAAACTTTTGATGTAAAAACCTAGGTG
E.c.  ATGGTCCAAGAATAGAGAGCTTGAAGTATCTTATGAAACATTTGATGTAAAAAATCAAGTA
A.m.  GAGGAGCCAGAGTGGAATTGGAAGCGAGCTACAGAAGTTTGCTACTTTGGCGACGGGC
       *   *   ****   **  **   **   * ****   **   *    **   ***
                                                              **

C.r.  GCAACTATAAAAACAACGCACACATGTACTGTGCTTTAGATACAGCAGCACAAAATAGCA
E.c.  ACAATTATAAGAATGAAGCACATAGATATTGTGCTCTATCCCATAACTCAGCAGCAGACA
A.m.  AGTACGCAAAAAGTG---------GTGCGGAATCTCTGGCAGCTATTACCCGCG
       *  *                                 *    *     *
       **                                      ****

C.r.  CTAAATGGCGCAGGATTAACTACATCTGTTATGTGTAAAAAACGAAAATTTAACAAATATAT
E.c.  TGAGTAGTGCAAG---TAATAATTTGTCTTTCTAAAAAATGAAGGATTACTTGACATAT
A.m.  ACGCTAACATTACTGAGACCAATTACTTCGTAGTACTTCAAAATTGATGAAATCACAAACACCT
       *   *   *    **    *  *    * *  *   * **    ** * *     *
                                       *****

C.r.  CATTAATGTTAAATGCGTGTTATGATATCATGCTTGATGGAATACCAGTTTCTCCATATG
E.c.  CATTTATGCGAACGCATGCTATGCTAGTAGTAGGCCGAAGGCATACCTTTTTCTCCTTATA
A.m.  CAGTCATGTTAAATGGCTGCTATGACGTGCTATGACGGTTTACCTGTCCCGTATG
       *   ** *    *  **    **      *      **    ** *  ** * ***
        **  *         *   **                *     * **  ***

C.r.  TATGTGCAGGTATTGGCACTGACTTAGTGTCAGTAATTAATGCTACAAATCCTAAATTAT
E.c.  TATGCGCAGGTATCGGTTACTGATTAGTATCCATGTTTGAAGCTACAAATCCTAAAATTT
A.m.  TATGTGCCGGGATAGGCGCAAGCTTTGTTGACATCTCTAAGCAAGTAACCACAAAGCTGG
       ****   **  **  **   *   * *  * **        *   *  *     *
                        *             **                   *

C.r.  CTTATCAAGGAAAGCTAGGCATAAGTTACTCAATCAATTCTGAAGCTTCTATCTTTATCG
E.c.  CTTACCAAGGAAAGTTAGGTTAAGTTTAAGCTACTCTATAAGCCCAGAAGCTTCTGTGTTATTG
A.m.  CCTACAGGGGCAAGGTTGGGATTAGCTTACCAGTTACTACCAGTTTACTCCGAAATATCCTTGGTGCAG
       ** *  **   **     **   **        *   *   **  *  **   *
         *   ***     *  **  * *   **   *   *  ***        ***

```
C.r.  GTGGACATTCCCATAGAGTTATAGGTAATGAATTTAAAGATATATTGCTACCTTAAAAATAT
E.c.  GTGGGCACTTTCATAAGGTAATAGGGAACGAATTTAGAGATATTCCTACTATAATACCTA
A.m.  GTGGGTTCTACCACGGGGCTATTTGATGAGTCTTACAAGGACATTCCCGCACACAACAGTG
      ****   *   *      * *** *   *  **  ** ***    *   *    *

C.r.  TTACTTCAAAAAACAGGAATATCTAATCCTGGCTTTGCATCAGCAACACTTGATGTTTGTC
E.c.  CTGGATCAACACTTGCAGGAAAAGAAACTACCCTGCAATAGTAATACTGGATGTATGCC
A.m.  TAAAGTTCTCTGGAGAAGCAAAA------------GCCTCAGTCAAAGCGCATATTGCTG
        *    *  *  *  **  *        **          **  *    **   *   **

C.r.  ACTTTGGTATAGAAATTGGGAGGAAGGTTTGTATTTTAA---
E.c.  ACTTTGGAATAGAAATGGGGAGGAAGGTTTAA---------
A.m.  ACTACGGCTTTAACCTTGGAGCAAGATTCCTGTTCAGCTAA
      ***  **   *  *  * *  ***  ***         **
```

```
  1 ggaatgaattcagggacatttctactcttaaagcgtttgctacaccatcatctgcagcta
    N  E  F  R  D  I  S  T  L  K  A  F  A  T  P  S  S  A  A  T
 61 ctccagacttagcaacagtaacactgagtgtgtgtcactttggagtagaacttggaggaa
    P  D  L  A  T  V  T  L  S  V  C  H  F  G  V  E  L  G  G  R
121 gatttaacttctaattttattattgccacatgttaaaaataatctaaacttgttttcatt
    F  N  F  *
181 attgctacaaatnaaataaaatagtggcaaaaaatgtagcaataagaggggggggggga
241 ctaattactatctgccatatcccttactaccacttacactaaataatctgacaaatacaa
301 cagcttctggagaaataaacaatatttaaattttcttacaaaaaccatttatatcttgt
                                                    -35
361 actaaaaactagcttataacttgttttttacattgtaggtttactactgttaatttgtttt
                    -10
421 cactatttcaggtgtaatatgaactgcgaaaaattttttataacaactgcattaacatta
             RBS      M  N  C  E  K  F  F  I  T  T  A  L  T  L
481 ctaatgtccttcttacctggaatatcactttctgatccagtgcaggatgacaacattagt
    L  M  S  F  L  P  G  I  S  L  S  D  P  V  Q  D  D  N  I  S
541 ggtaatttctacatcagtggaaagtatatgccaagcgcttcgcattttggagttttttct
    G  N  F  Y  I  S  G  K  Y  M  P  S  A  S  H  F  G  V  F  S
601 gccaaggaagaaagaaatacaacagttggagtatttggaatagagcaagattgggataga
    A  K  E  E  R  N  T  T  V  G  V  F  G  I  E  Q  D  W  D  R
661 tgtgtaatactagaaccacttaagcgatatattcaccgttccaaattattcatttaag
    C  V  I  S  R  T  T  L  S  D  I  F  T  V  P  N  Y  S  F  K
721 tatgaaataatctattttcaggatttgcaggagctattggctactcaatggatggccca
    Y  E  N  N  L  F  S  G  F  A  G  A  I  G  Y  S  M  D  G  P
781 agaatagagcttgaagtatctTatgaagcattcgatgttaaaaatcaaggtaacaattat
    R  I  E  L  E  V  S  Y  E  A  F  D  V  K  N  Q  G  N  N  Y
841 aagaacgaagcacatagatattatgctctgtcccatcttctcggcacagagacacagata
    K  N  E  A  H  R  Y  Y  A  L  S  H  L  L  G  T  E  T  Q  I
901 gatggtgcaggcagtgcgtctgtctttctaataaatgaaggactacttgataaatcattt
    D  G  A  G  S  A  S  V  F  L  I  N  E  G  L  L  D  K  S  F
961 atgctaacgcatgttatgatgtaataagtgaaggcataccttttctcccttatatatgt
    M  L  N  A  C  Y  D  V  I  S  E  G  I  P  F  S  P  Y  I  C
1021 gcaggtattggtattgatttagtatccatgtttgaagctataaatccaaaatttcttat
     A  G  I  G  I  D  L  V  S  M  F  E  A  I  N  P  K  I  S  Y
1081 caaggaaaattaggcttaagttaccctataagcccagaagcttctgtgtttattggtgga
     Q  G  K  L  G  L  S  Y  P  I  S  P  E  A  S  V  F  I  G  G
1141 cattttcataaggtgataggaaacgaatttagagatattcctactatgataccttgtgaa
     H  F  H  K  V  I  G  N  E  F  R  D  I  P  T  M  I  P  S  E
1201 tcagcgcttgcaggaaaaggaaactaccctgcaatagtaacactggacgtgttctacttt
     S  A  L  A  G  K  G  N  Y  P  A  I  V  T  L  D  V  F  Y  F
1261 ggcatagaacttggaggaaggtttaacttccaactttgattattgccacaataaataaaa
     G  I  E  L  G  G  R  F  N  F  Q  L  *
1321 atagtggcaaaagaatgtagcaataagagggggggagggggaactaaattattatttgcc
1381 atatcccttactaccacttacaccaaataatctgacaaatacaacagttcaaacaaggt
1441 aaacaattcttaaattttgtcttatgagaaccattgatatcttatattaaaaactagctta
                                        -35
1501 taacttgtctttacattgcagttctactattgttaatttattttcactattttaggtgta
     -10                                                    RBS
1561 atatgaattgcaaaaaattttttataacaactgcattagtatcactaatgtccttctac
     M  N  C  K  K  F  F  I  T  T  A  L  V  S  L  M  S  F  L  P
1621 ctggaatatcattttctgatccagtgcaaggtgacaatattagtggtaatttctatgtta
     G  I  S  F  S  D  P  V  Q  G  D  N  I  S  G  N  F  Y  V  S
1681 gtggcaagtatatgccaagtgcttcgcattttggcatgttttctgccaaagaagaaaaa
     G  K  Y  M  P  S  A  S  H  F  G  M  F  S  A  K  E  E  K  N
1741 atcctactgttgcattgtatggcttaaaacaagattgggaagggattagctcatcaagtc
     P  T  V  A  L  Y  G  L  K  Q  D  W  E  G  I  S  S  S  S  H
1801 acaatgataatcatttcaataacaagggttattcatttaaatatgaaaataacccatttt
     N  D  N  H  F  N  N  K  G  Y  S  F  K  Y  E  N  N  P  F  L
1861 tagggtttgcaggagctattggttattcaatgggtggtccaagagtagagtttgaagtgt
     G  F  A  G  A  I  G  Y  S  M  G  G  P  R  V  E  F  E  V  S
1921 cctatgaaacatttgacgttaaaaatcagggtaataactataaaaatgatgctcacagat
     Y  E  T  F  D  V  K  N  Q  G  N  N  Y  K  N  D  A  H  R  Y
1981 actgctctttaggtcaacaagacaacagcggaatacctaaaactagtaaatacgtactgt
     C  A  L  G  Q  Q  D  N  S  G  I  P  K  T  S  K  Y  V  L  L
2041 taaaaagcgaaggattgcttgacatatcatttatgctaaatgcatgctatgatataataa
     K  S  E  G  L  L  D  I  S  F  M  L  N  A  C  Y  D  I  I  N
2101 acgagagcataccttttgtctccttacatatgtgcaggtgttggtActgattttaatatcca
     E  S  I  P  L  S  P  Y  I  C  A  G  V  G  T  D  L  I  S  M
2161 tgtttgaagctacaaatccaaaatttcttaccaagggaagttaggtctaagttactcta
     F  E  A  T  N  P  K  I  S  Y  Q  G  K  L  G  L  S  Y  S  I
2221 taaacccagaagcttctgtatttattggtggacattttcataaggtgataggaaacgaat
     N  P  E  A  S  V  F  I  G  G  H  F  H  K  V  I  G  N  E  F
2281 ttagggacattcctactctgaaagcatttgttacgtcatcagctactccagatctagcaa
     R  D  I  P  T  L  K  A  F  V  T  S  S  A  T  P  D  L  A  I
```

FIG. 2A

```
2341 tagtaacactaagtgtatgtcattttggaatagaacttggaggaaggtttaacttctaat
      V  T  L  S  V  C  H  F  G  I  E  L  G  G  R  F  N  F  *
2401 tttgttattgccacatgttaaaaataatctaaacttgttttcattattgctacagtaaat
2461 aaaaatagtggcaaaagaatgtagcaataagaagggggggggggactaaattgctattt
2521 accatatcccttattataccacttacactaaataacttgacaaatacaacagcttctgga
2581 aaaacaaacaatacttaaatttctcttacaaaaaccatttatatcttgtactaaaaacta
                                              -35
2641 gcttataacttgttttacattgtagttctactattgttaatttatttcactattttag
        -10                                                    
2701 gtgcaatatgaattgcaaaaatttttataacaactacattagtatcgctaatgtcctt
     RBS M  N  C  K  K  F  F  I  T  T  T  L  V  S  L  M  S  F
2761 cttacctggaatatcattttctgatgcagtacagaacgacaatgttggtggtaatttcta
     L  P  G  I  S  F  S  D  A  V  Q  N  D  N  V  G  G  N  F  Y
2821 tatcagtgggaaatatgtaccaagtgtttcacattttggcgtattctctgctaaacagga
     I  S  G  K  Y  V  P  S  V  S  H  F  G  V  F  S  A  K  Q  E
2881 aagaaatacaacaatcggagtatttggattaaagcaagattgggatggcagcacaatatc
     R  N  T  T  I  G  V  F  G  L  K  Q  D  W  D  G  S  T  I  S
2941 taaaaattctccagaaaatacatttaacgttccaaattattcatttaaatatgaaaataa
     K  N  S  P  E  N  T  F  N  V  P  N  Y  S  F  K  Y  E  N  N
3001 tccatttctaggttttgcaggagctgttggttatttaatgaatggtccaagaatagagtt
     P  F  L  G  F  A  G  A  V  G  Y  L  M  N  G  P  R  I  E  L
3061 agaaatgtcctatgaaacatttgatgtgaaaaaccagggtaataactataagaacgatgc
     E  M  S  Y  E  T  F  D  V  K  N  Q  G  N  N  Y  K  N  D  A
3121 tcacaaatattatgctttaacccataacagtgggggaaagctaagcaatgcaggtgataa
     H  K  Y  Y  A  L  T  H  N  S  G  G  K  L  S  N  A  G  D  K
3181 gtttgttttctaaaaaatgaaggacttctgatatcacttatgttgaatgcatgcta
     V  F  V  L  K  N  E  G  L  L  D  I  S  L  M  L  N  A  C  Y
3241 tgatgtaataagtgaaggaataccttctctccttacatatgtgcaggtgttggtactga
     D  V  I  S  E  G  I  P  F  S  P  Y  I  C  A  G  V  G  T  D
3301 tttaatatccatgtttgaagctataaaccctaaaatttcttatcaaggaaagttaggttt
     L  I  S  M  F  E  A  I  N  P  K  I  S  Y  Q  G  K  L  G  L
3361 gagttactccataagcccagaagcttctgtttttgttggtggacattttcataaggtgat
     S  Y  S  I  S  P  E  A  S  V  F  V  G  G  H  F  H  K  V  I
3421 agggaatgaattcagagatattcctgctatgatacccagtacctcaactctcacaggtaa
     G  N  E  F  R  D  I  P  A  M  I  P  S  T  S  L  T  G  N
3481 tcactttactatagtaacactaagtgtatgccactttggagtggaacttggaggaaggtt
     H  F  T  I  V  T  L  S  V  C  H  F  G  V  E  L  G  G  R  F
3541 taacttttaattttattattgccacatgttaaaaataatctaaacttgttttattattg
     N  F  *
3601 ctgcaggtaaataaaaatagtggcaaaagaatgtagcaataagagggggggggggactag
3661 tttataagtgctgttttctcacctttacacatgatactatacttaaccagttttttttgc
3721 tattacttacctgacgtaatatattaaattttccttacaaaagttaccgatattttatac
                                                     -35
3781 aaaaatttatattctgacttgcttttatatgacacttctactattgttaatttatttgtc
            -10
3841 actattaggttatatatgaattacaaaaaagttttcataacaagtgcattgatatcatta
     RBS        M  N  Y  K  K  V  F  I  T  S  A  L  I  S  L
3901 atatcttctctacctggagtatcattttccgacccagcaggtagtggtattaacggtaat
     I  S  S  L  P  G  V  S  F  S  D  P  A  G  S  G  I  N  G  N
3961 ttctacatcagtggaaaatacatgccaagtgcttcgcattttggagtattctctgctaag
     F  Y  I  S  G  K  Y  M  P  S  A  S  H  F  G  V  F  S  A  K
4021 gaagaaagaaatacaacagttggagtgtttggactgaagcaaaattgggacggaagcgca
     E  E  R  N  T  T  V  G  V  F  G  L  K  Q  N  W  D  G  S  A
4081 atatccaactcctccccaaacgatgtattcactgtctcaaattattcatttaaatatgaa
     I  S  N  S  S  P  N  D  V  F  T  V  S  N  Y  S  F  K  Y  E
4141 aacaaccgttttaggttttgcaggagctattggttactcaatggatggtccaagaata
     N  N  P  F  L  G  F  A  G  A  I  G  Y  S  M  D  G  P  R  I
4201 gagcttgaagtatcttatgaaacatttgatgtaaaaaatcaaggtaacaattataagaat
     E  L  E  V  S  Y  E  T  F  D  V  K  N  Q  G  N  N  Y  K  N
4261 gaagcacatagatattgtgctctatcccataactcagcagcagacatgagtagtgcaagt
     E  A  H  R  Y  C  A  L  S  H  N  S  A  A  D  M  S  S  A  S
4321 aataattttgtctttctaaaaaatgaaggattacttgacatatcatttatgctgaacgca
     N  N  F  V  F  L  K  N  E  G  L  L  D  I  S  F  M  L  N  A
4381 tgctatgacgtagtaggcgaaggcataccttttctccttatatgcgcaggtatcggt
     C  Y  D  V  V  G  E  G  I  P  F  S  P  Y  I  C  A  G  I  G
4441 actgatttagtatccatgtttgaagctacaaatccctaaaatttcttaccaaggaaagtta
     T  D  L  V  S  M  F  E  A  T  N  P  K  I  S  Y  Q  G  K  L
4501 ggtttaagctactctataagcccagaagcttctgtgtttattggtgggcactttcataag
     G  L  S  Y  S  I  S  P  E  A  S  V  F  I  G  G  H  F  H  K
4561 gtaatagggaacgaatttagagatattcctactataatacctactggatcaacacttgca
     V  I  G  N  E  F  R  D  I  P  T  I  I  P  T  G  S  T  L  A
4621 ggaaaaggaaactaccctgcaatagtaatactggatgtatgccactttggaatagaaatg
     G  K  G  N  Y  P  A  I  V  I  L  D  V  C  H  F  G  I  E  M
4681 gga
     G
```

FIG. 2B

```
   1 tggtgtaaatatgaaatataaaaaacttttacagtaactgcattagtattattaacttc
     RBS      M  K  Y  K  K  T  F  T  V  T  A  L  V  L  L  T  S
  61 ctttacacatttataccttttatagtccagcacgtgccagtacaattcacaacttcta
      F  T  H  F  I  P  F  Y  S  P  A  R  A  S  T  I  H  N  F  Y
 121 cattagtggaaaatatatgccaacagcgtcacattttggaattttttcagctaaagaaga
      I  S  G  K  Y  M  P  T  A  S  H  F  G  I  F  S  A  K  E  E
 181 acaaagttttactaaggtattagttgggttagatcaacgattatcacataatattataaa
      Q  S  F  T  K  V  L  V  G  L  D  Q  R  L  S  H  N  I  I  N
 241 caataatgatacagcaaagagtcttaaggttcaaaattattcatttaaatacaaaaataa
      N  N  D  T  A  K  S  L  K  V  Q  N  Y  S  F  K  Y  K  N  N
 301 cccatttctaggatttgcaggagctattggttattcaataggcaattcaagaatagaact
      P  F  L  G  F  A  G  A  I  G  Y  S  I  G  N  S  R  I  E  L
 361 agaagtatcacatgaaatatttgatactaaaaacccaggaaacaattatttaaatgactc
      E  V  S  H  E  I  F  D  T  K  N  P  G  N  N  Y  L  N  D  S
 421 tcacaaatattgcgctttatctcatggaagtcacatatgcagtgatggaaatagcggaga
      H  K  Y  C  A  L  S  H  G  S  H  I  C  S  D  G  N  S  G  D
 481 ttggtacactgcaaaaactgataagtttgtacttctgaaaaatgaaggtttacttgacgt
      W  Y  T  A  K  T  D  K  F  V  L  L  K  N  E  G  L  L  D  V
 541 ctcatttatgttaaacgcatgttatgacataacaactgaaaaaatgcctttttcacctta
      S  F  M  L  N  A  C  Y  D  I  T  T  E  K  M  P  F  S  P  Y
 601 tatatgtgcaggtattggtactgatctcatatctatgtttgagacaacacaaaacaaaat
      I  C  A  G  I  G  T  D  L  I  S  M  F  E  T  T  Q  N  K  I
 661 atcttatcaaggaaagttaggtttaaactatactataaactcaagagtttctgttttgc
      S  Y  Q  G  K  L  G  L  N  Y  T  I  N  S  R  V  S  V  F  A
 721 aggtgggcactttcataaggtaataggtaatgaatttaaaggtattcctactctattacc
      G  G  H  F  H  K  V  I  G  N  E  F  K  G  I  P  T  L  L  P
 781 tgatggatcaaacattaaagtacaacagtctgcaacagtaacattagatgtgtgccattt
      D  G  S  N  I  K  V  Q  Q  S  A  T  V  T  L  D  V  C  H  F
 841 cgggttagagattggaagtagattttcttttaatacttctattgtacatgttaaaaata
      G  L  E  I  G  S  R  F  F  F  *
 901 gtactagtttgcttctgtggtttataaacgcaagagagaaatagttagtaataaattaga
 961 aagttaaatattagaaaagtcatatgttttcattgtcattgatactcaactaaaagtag
1021 tataaatgttacttattaataattttacgtagtatattaaatttcccttacaaaagccac
1081 tagtattttatactaaaagctatactttggcttgtatttaatttgtattttactactgt
       -35                         -10
1141 taatttactttcactgtttctggtgtaaatatgaattgtaaaaagttttcacaataagt
                         RBS      M  N  C  K  K  V  F  T  I  S
1201 gcattgatatcatccatatacttcctacctaatgtctcatactctaacccagtatatggt
      A  L  I  S  S  I  Y  F  L  P  N  V  S  Y  S  N  P  V  Y  G
1261 aacagtatgtatggtaattttacatatcaggaaagtacatgccaagtgttcctcattt
      N  S  M  Y  G  N  F  Y  I  S  G  K  Y  M  P  S  V  P  H  F
1321 ggaattttttcagctgaagaagagaaaaaaaagacaactgtagtatatggcttaaaagaa
      G  I  F  S  A  E  E  E  K  K  K  T  T  V  V  Y  G  L  K  E
1381 aactgggcaggagatgcaatatctagtcaaagtccagatgataatttaccattcgaaat
      N  W  A  G  D  A  I  S  S  Q  S  P  D  D  N  F  T  I  R  N
1441 tactcattcaagtatgcaagcaacaagttttagggttgcagtagctattggttactcg
      Y  S  F  K  Y  A  S  N  K  F  L  G  F  A  V  A  I  G  Y  S
1501 ataggcagtccaagaatagaagttgagatgtcttatgaagcatttgatgtaaaaaatcaa
      I  G  S  P  R  I  E  V  E  M  S  Y  E  A  F  D  V  K  N  Q
1561 ggtaacaatt
      G  N  N
```

FIG. 2C

```
  1   acatgtatacattatagtaacaaatgttaccgtatttttattcataagttaagtaaaatct
 61   ataccattctctttcactttatcagaagacttttatttatcacaaactcatgacgtatag
121   tgtcacaaataaacacactgcaactgcaatcactacgtaaaactttaactcttcttttc
181   acaactaaatactaataaaagtaatatagtataaaaaatcttaagtaacTTGACAtaat
                                                      -35
241   attactctgataTAGCATatgtctagtatctctatactaaacgtttatataattGGAGca
                  -10
301   tattaATGAAAGCTATCAAATTCATACTTAATGTCTGCTTACTATTTGCAGCAATATTTT
          M   K   A   I   K   F   I   L   N   V   C   L   L   F   A→  A   I   F   L
361   TAGGGTATTCCTATATTACAAAACAAGGCATATTTCAAACAAAACATCATGATACACCTA
        G   Y   S   Y   I   T   K   Q   G   I   F   Q   T   K   H   H   D   T   P   N
421   ATACTACTATACCAAATGAAGACGGTATTCAATCTAGCTTTAGCTTAATCAATCAAGACG
          T   T   I   P   N   E   D   G   I   Q   S   S   F   S   L   I   N   Q   D
481   GTAAAACAGTAACCAGCCAAGATTTCCTAGGGAAACACATGTTAGTTTTGTTTGGATTCT
        G   K   T   V   T   S   Q   D   F   L   G   K   H   M   L   V   L   F   G   F   S
541   CTGCATGTAAAAGCATTTGCCCTGCAGAATTGGGATTAGTATCTGAAGCACTTGCACAAC
          A   C   K   S   I   C   P   A   E   L   G   L   V   S   E   A   L   A   Q   L
601   TTGGTAATAATGCAGACAAATTACAAGTAATTTTTATTACAATTGATCCAAAAAATGATA
        G   N   N   A   D   K   L   Q   V   I   F   I   T   I   D   P   K   N   D   T
661   CTGTAGAAAAATTAAAAGAATTTCATGAACATTTTGATTCAAGAATTCAAATGTTAACAG
          V   E   K   L   K   E   F   H   E   H   F   D   S   R   I   Q   M   L   T   G
721   GAAATACTGAAGACATTAATCAAATAATTAAAAATTATAAAATATATGTTGGACAAGCAG
        N   T   E   D   I   N   Q   I   I   K   N   Y   K   I   Y   V   G   Q   A   D
781   ATAAAGATCATCAAATTAACCATTCTGCAATAATGTACCTTATTGACAAAAAAGGATCAT
          K   D   H   Q   I   N   H   S   A   I   M   Y   L   I   D   K   K   G   S   Y
841   ATCTTTCACACTTCATTCCAGATTTAAAATCACAAGAAAATCAAGTAGATAAGTTACTAT
        L   S   H   F   I   P   D   L   K   S   Q   E   N   Q   V   D   K   L   L   S
901   CTTTAGTTAAGCAGTATCTGTAAtttaataattaattAAAGagaatagtacacaCTTTtt
          L   V   K   Q   Y   L   *
961   ataaattcatggaatacgttggatgagtaggttttttttagtatttttagtgctaataac
1021  attggcat
```

FIG. 3A

```
  1    ggaaatctcatgtaaacgtgaaatactatattctttttaaataccaatacaattgaata 61    caaaaaacttttacaacttattatgtttatcttaaaaccttatttaagattccttatg 121    tcacaaataacaaaatactatttacaaaatacaccacaatttcatcaaataaaaaaaa 181    ctatacactttattatactacagtagatataccataaaagattttaagtaacTTGACAta
                                                          ‾‾‾‾‾‾
                                                           -35
241    atattaccttggtaTAGCATatgattcagtattttatattaaaatttattatgtattGGA
                     ‾‾‾‾‾‾                                      ‾‾‾
                      -10
301    GcataaaATGAAAGTTATCAAATTTATACTTAATATCTGTTTATTATTTGCAGCAATTTT
       ‾        M  K  V  I  K  F  I  L  N  I  C  L  L  F  A →A  I  F 361    TCTAGGATATTCCTACGTAACAAAACAAGGCATTTTTCAAGTAAGAGATCATAACACTCC
        L  G  Y  S  Y  V  T  K  Q  G  I  F  Q  V  R  D  H  N  T  P 421    CAATACAAATATATCAAATAAAGCCAGCATTACTACTAGTTTTTCGTTAGTAAATCAAGA
        N  T  N  I  S  N  K  A  S  I  T  T  S  F  S  L  V  N  Q  D 481    TGGAAATACAGTAAATAGTCAAGATTTTTTGGGAAAATACATGCTAGTTTTATTTGGATT
        G  N  T  V  N  S  Q  D  F  L  G  K  Y  M  L  V  L  F  G  F 541    TTCTTCATGTAAAAGCATCTGCCCTGCTGAATTAGGAATAGCATCTGAAGTTCTCTCACA
        S  S  C  K  S  I  C  P  A  E  L  G  I  A  S  E  V  L  S  Q 601    GCTTGGTAATGACACAGACAAGTTACAAGTAATTTTCATTACAATTGATCCAACAAATGA
        L  G  N  D  T  D  K  L  Q  V  I  F  I  T  I  D  P  T  N  D 661    TACTGTACAAAAATTAAAAACATTTCATGAACATTTTGATCCTAGAATTCAAATGCTAAC
        T  V  Q  K  L  K  T  F  H  E  H  F  D  P  R  I  Q  M  L  T 721    AGGCAGTGCAGAAGATATTGAAAAAATAATAAAAAATTACAAAATATATGTTGGACAAGC
        G  S  A  E  D  I  E  K  I  I  K  N  Y  K  I  Y  V  G  Q  A 781    AGATAAAGATAATCAAATTGATCACTCTGCCATAATGTACATTATCGATAAAAAAGGAGA
        D  K  D  N  Q  I  D  H  S  A  I  M  Y  I  I  D  K  K  G  E 841    ATACATTTCACACTTTTCTCCAGATTTAAAATCAACAGAAAATCAAGTAGATAAGTTACT
        Y  I  S  H  F  S  P  D  L  K  S  T  E  N  Q  V  D  K  L  L 901    ATCTATAATAAAACAATATCTCTAAtttaataattaattaAAGAGaatagtacacaCTCT
        S  I  I  K  Q  Y  L  *                ‾‾‾‾‾               ‾‾‾‾

961    Tatataaattcatggatatatgtgatgggtagatttcttttggtgtttctatcgctaatt
       ‾
1021   acatta
```

FIG. 3B

NUCLEIC ACID VACCINES AGAINST RICKETTSIAL DISEASES AND METHODS OF USE

CROSS-REFERENCE TO RELATED APPLICATIONS

This application is a continuation-in-part of Ser. No. 09/337,827, filed Jun. 22, 1999 now abandoned; which is a divisional of Ser. No. 08/953,326, filed Oct. 17, 1997, now U.S. Pat. No. 6,251,872; which is a continuation-in-part of application Ser. No. 08/733,230, filed Oct. 17, 1996, now U.S. Pat. No. 6,025,338. This application also claims priority from provisional application Ser. No. 60/130,725, filed Apr. 22, 1999.

This invention was made with government support under USAID Grant No. LAG-1328-G-00-3030-00. The government has certain rights in this invention.

TECHNICAL FIELD

This invention relates to nucleic acid vaccines for rickettsial diseases of animals, including humans.

BACKGROUND OF THE INVENTION

The rickettsias are a group of small bacteria commonly transmitted by arthropod vectors to man and animals, in which they may cause serious disease. The pathogens causing human rickettsial diseases include the agent of epidemic typhus, *Rickettsia prowazekii*, which has resulted in the deaths of millions of people during wartime and natural disasters. The causative agents of spotted fever, e.g., *Rickettsia rickettsii* and *Rickettsia conorii*, are also included within this group. Recently, new types of human rickettsial disease caused by members of the tribe Ehrlichiae have been described. Ehrlichiae infect leukocytes and endothelial cells of many different mammalian species, some of them causing serious human and veterinary diseases. Over 400 cases of human ehrlichiosis, including some fatalities, caused by *Ehrlichia chaffeensis* have now been reported. Clinical signs of human ehrlichiosis are similar to those of Rocky Mountain spotted fever, including fever, nausea, vomiting, headache, and rash.

Heartwater is another infectious disease caused by a rickettsial pathogen, namely *Cowdria ruminantium*, and is transmitted by ticks of the genus Amblyomma. The disease occurs throughout most of Africa and has an estimated endemic area of about 5 million square miles. In endemic areas, heartwater is a latent infection in indigenous breeds of cattle that have been subjected to centuries of natural selection. The problems occur where the disease contacts susceptible or naive cattle and other ruminants. Heartwater has been confirmed to be on the island of Guadeloupe in the Caribbean and is spreading through the Caribbean Islands. The tick vectors responsible for spreading this disease are already present on the American mainland and threaten the livestock industry in North and South America.

In acute cases of heartwater, animals exhibit a sudden rise in temperature, signs of anorexia, cessation of rumination, and nervous symptoms including staggering, muscle twitching, and convulsions. Death usually occurs during these convulsions. Peracute cases of the disease occur where the animal collapses and dies in convulsions having shown no preliminary symptoms. Mortality is high in susceptible animals. Angora sheep infected with the disease have a 90% mortality rate while susceptible cattle strains have up to a 60% mortality rate.

If detected early, tetracycline or chloramphenicol treatment are effective against rickettsial infections, but symptoms are similar to numerous other infections and there are no satisfactory diagnostic tests (Helmick, C., K. Bernard, L. D'Angelo [1984] *J. Infect. Dis.* 150:480).

Animals which have recovered from heartwater are resistant to further homologous, and in some cases heterologous, strain challenge. It has similarly been found that persons recovering from a rickettsial infection may develop a solid and lasting immunity. Individuals recovered from natural infections are often immune to multiple isolates and even species. For example, guinea pigs immunized with a recombinant *R. conorii* protein were partially protected even against *R. rickettsii* (Vishwanath, S., G. McDonald, N. Watkins [1990] *Infect. Immun.* 58:646). It is known that there is structural variation in rickettsial antigens between different geographical isolates. Thus, a functional recombinant vaccine against multiple isolates would need to contain multiple epitopes, e.g., protective T and B cell epitopes, shared between isolates. It is believed that serum antibodies do not play a significant role in the mechanism of immunity against rickettsia (Uilenberg, G. [1983] *Advances in Vet. Sci. and Comp. Med.* 27:427–480; Du Plessis, Plessis, J. L. [1970] *Onderstepoort J. Vet. Res.* 37(3):147–150).

Vaccines based on inactivated or attenuated rickettsiae have been developed against certain rickettsial diseases, for example against *R. prowazekii* and *R. rickettsii*. However, these vaccines have major problems or disadvantages, including undesirable toxic reactions, difficulty in standardization, and expense (Woodward, T. [1981] "Rickettsial diseases: certain unsettled problems in their historical perspective," In Rickettsia and Rickettsial Diseases, W. Burgdorfer and R. Anacker, eds., Academic Press, New York, pp. 17–40).

A vaccine currently used in the control of heartwater is composed of live infected sheep blood. This vaccine also has several disadvantages. First, expertise is required for the intravenous inoculation techniques required to administer this vaccine. Second, vaccinated animals may experience shock and so require daily monitoring for a period after vaccination. There is a possibility of death due to shock throughout this monitoring period, and the drugs needed to treat any shock induced by vaccination are costly. Third, blood-borne parasites may be present in the blood vaccine and be transmitted to the vaccinates. Finally, the blood vaccine requires a cold chain to preserve the vaccine.

Clearly, a safer, more effective vaccine that is easily administered would be particularly advantageous. For these reasons, and with the advent of new methods in biotechnology, investigators have concentrated recently on the development of new types of vaccines, including recombinant vaccines. However, recombinant vaccine antigens must be carefully selected and presented to the immune system such that shared epitopes are recognized. These factors have contributed to the search for effective vaccines.

A protective vaccine against rickettsiae that elicits a complete immune response can be advantageous. A few antigens which potentially can be useful as vaccines have now been identified and sequenced for various pathogenic rickettsia. The genes encoding the antigens and that can be employed to recombinantly produce those antigen have also been identified and sequenced. Certain protective antigens identified for *R. rickettsi*, *R. conorii*, and *R. prowazekii* (e.g., rOmpA and rOmpB) are large (>100 kDa), dependent on retention of native conformation for protective efficacy, but are often degraded when produced in recombinant systems.

This presents technical and quality-control problems if purified recombinant proteins are to be included in a vaccine. The mode of presentation of a recombinant antigen to the immune system can also be an important factor in the immune response.

Nucleic acid vaccination has been shown to induce protective immune responses in non-viral systems and in diverse animal species (Special Conference Issue, WHO meeting on nucleic acid vaccines [1994] *Vaccine* 12:1491). Nucleic acid vaccination has induced cytotoxic lymphocyte (CTL), T-helper 1, and antibody responses, and has been shown to be protective against disease (Ulmer, J., J. Donelly, S. Parker et al. [1993] *Science* 259:1745). For example, direct intramuscular injection of mice with DNA encoding the influenza nucleoprotein caused the production of high titer antibodies, nucleoprotein-specific CTLs, and protection against viral challenge. Immunization of mice with plasmid DNA encoding the *Plasmodium yoelii* circumsporozoite protein induced high antibody titers against malaria sporozoites and CTLs, and protection against challenge infection (Sedegah, M., R. Hedstrom, P. Hobart, S. Hoffman [1994] *Proc. Natl. Acad. Sci. USA* 91:9866). Cattle immunized with plasmids encoding bovine herpesvirus 1 (BHV-1) glycoprotein IV developed neutralizing antibody and were partially protected (Cox, G., T. Zamb, L. Babiuk [1993] *J. Virol.* 67:5664). However, it has been a question in the field of immunization whether the recently discovered technology of nucleic acid vaccines can provide improved protection against an antigenic drift variant. Moreover, it has not heretofore been recognized or suggested that nucleic acid vaccines may be successful to protect against rickettsial disease or that a major surface protein conserved in rickettsia was protective against disease.

BRIEF SUMMARY OF THE INVENTION

Disclosed and claimed here are novel vaccines for conferring immunity to rickettsia infection, including *Cowdria ruminantium* causing heartwater. Also disclosed are novel nucleic acid compositions and methods of using those compositions, including to confer immunity in a susceptible host. Also disclosed are novel materials and methods for diagnosing infections by Ehrlichia humans or animals.

One aspect of the subject invention concerns a nucleic acid, e.g., DNA or mRNA, vaccine containing the major antigenic protein 1 gene (MAP1) or the major antigenic protein 2 gene (MAP2) of rickettsial pathogens. In one embodiment, the nucleic acid vaccines can be driven by the human cytomegalovirus (HCMV) enhancer-promoter. In studies immunizing mice by intramuscular injection of a DNA vaccine composition according to the subject invention, immunized mice seroconverted and reacted with MAP1 in antigen blots. Splenocytes from immunized mice, but not from control mice immunized with vector only, proliferated in response to recombinant MAP1 and rickettsial antigens in in vitro lymphocyte proliferation tests. In experiments testing different DNA vaccine dose regimens, increased survival rates as compared to controls were observed on challenge with rickettsia. Accordingly, the subject invention concerns the discovery that DNA vaccines can induce protective immunity against rickettsial disease or death resulting therefrom.

The subject invention further concerns the genes designated *Cowdria ruminantium* map 2, *Cowdria ruminantium* 1hworf3, *Cowdria ruminantium* 4hworf1, *Cowdria ruminantium* 18hworf1, and *Cowdria ruminantium* 3gdorf3 and the use of these genes in diagnostic and therapeutic applications. The subject invention further concerns the proteins encoded by the exemplified genes, antibodies to these proteins, and the use of such antibodies and proteins in diagnostic and therapeutic applications.

In one embodiment of the subject invention, the polynucleotide vaccines are administered in conjunction with an antigen. In a preferred embodiment, the antigen is the polypeptide which is encoded by the polynucleotide administered as the polynucleotide vaccine. As a particularly preferred embodiment, the antigen is administered as a booster subsequent to the initial administration of the polynucleotide vaccine.

BRIEF DESCRIPTION OF THE DRAWINGS

FIGS. 1A–1C show a comparison of the amino acid sequences from alignment of the three rickettsial proteins, namely, *Cowdria ruminantium* (*C.r.*), *Ehrlichia chaffeensis* (*E.c.*), and *Anaplasma marginale* (*A.m.*).

FIGS. 2A–2C shows the DNA sequence of the 28 kDa gene locus cloned from *E. chaffeensis* (FIGS. 2A–2B) and *E. canis* (FIG. 2C). One letter amino acid codes for the deduced protein sequences are presented below the nucleotide sequence. The proposed sigma-70-like promoter sequences (38) are presented in bold and underlined text as −10 and −35 (consensus −35 and −10 sequences are TTGACA and TATAAT, respectively). Similarly, consensus ribosomal binding sites and transcription terminator sequences (bold letter sequence) are identified. G-rich regions identified in the *E. chaffeensis* sequence are underlined. The conserved sequences from within the coding regions selected for RT-PCR assay are identified with italics and underlined text.

FIG. 3A shows the complete sequence of the MAP2homolog of *Ehrlichia canis*. The arrow (→) represents the predicted start of then mature protein. The asterisk (*) represents the stop codon. Underlined nucleotides 5' to the open reading frame with −35 and −10 below represent predicted promoter sequences. Double underlined nucleotides represent the predicted ribosomal binding site. Underlined nucleotides 3' to the open reading frame represent possible transcription termination sequences.

FIG. 3B shows the complete sequence of the MAP2 homolog of *Ehrlichia chaffeensis*. The arrow (→) represents the predicted start of the mature protein. The asterisk (*) represents the stop codon. Underlined nucleotides 5' to the open reading frame with −35 and −10 below represent predicted promoter sequences. Double underlined nucleotides represent the predicted ribosomal binding site. Underlined nucleotides 3' to the open reading frame represent possible transcription termination sequences.

BRIEF DESCRIPTION OF THE SEQUENCES

SEQ ID NO.1 is the coding sequence of the MAP1 gene from *Cowdria ruminantium* (Highway isolate).

SEQ ID NO.2 is the polypeptide encoded by the polynucleotide of SEQ ID NO. 1.

SEQ ID NO.3 is the coding sequence of the MAP1 gene from *Ehrlichia chaffeensis*.

SEQ ID NO.4 is the polypeptide encoded by the polynucleotide of SEQ ID NO.3.

SEQ ID NO.5 is the *Anaplasma marginale* MSP4 gene coding sequence.

SEQ ID NO.6 is the polypeptide encoded by the polynucleotide of SEQ ID NO.5.

SEQ ID NO. 7 is a partial coding sequence of the VSA1 gene from *Ehrlichia chaffeensis*, also shown in FIGS. 2A–2B.

SEQ ID NO.8 is the coding sequence of the VSA2 gene from *Ehrlichia chaffeensis*, also shown in FIGS. 2A–2B.

SEQ ID NO.9 is the coding sequence of the VSA3 gene from *Ehrlichia chaffeensis*, also shown in FIGS. 2A–2B.

SEQ ID NO. 10 is the coding sequence of the VSA4 gene from *Ehrlichia chaffeensis*, also shown in FIGS. 2A–2B.

SEQ ID NO. 11 is a partial coding sequence of the VSA5 gene from *Ehrlichia chaffeensis*, also shown in FIGS. 2A–2B.

SEQ ID NO.12 is the coding sequence of the VSA1 gene from *Ehrlichia canis*, also shown in FIG. 2C.

SEQ ID NO.13 is a partial coding sequence of the VSA2 gene from *Ehrlichia canis*, also shown in FIG. 2C.

SEQ ID NO.14 is the polypeptide encoded by the polynucleotide of SEQ ID NO. 7, also shown in FIGS. 2A–2B.

SEQ ID NO.15 is the polypeptide encoded by the polynucleotide of SEQ ID NO. 8, also shown in FIGS. 2A–2B.

SEQ ID NO.16 is the polypeptide encoded by the polynucleotide of SEQ ID NO. 9, also shown in FIGS. 2A–2B.

SEQ ID NO.17 is the polypeptide encoded by the polynucleotide of SEQ ID NO. 10, also shown in FIGS. 2A–2B.

SEQ ID NO.18 is the polypeptide encoded by the polynucleotide of SEQ ID NO. 11, also shown in FIGS. 2A–2B.

SEQ ID NO.19 is the polypeptide encoded by the polynucleotide of SEQ ID NO. 12, also shown in FIG. 2C.

SEQ ID NO.20 is the polypeptide encoded by the polynucleotide of SEQ ID NO. 13, also shown in FIG. 2C.

SEQ ID NO.21 is the coding sequence of the MAP2 gene from *Ehrlichia canis*, also shown in FIG. 3A.

SEQ ID NO. 22 is the coding sequence of the MAP2 gene from *Ehrlichia chaffeensis*, also shown in FIG. 3B.

SEQ ID NO.23 is the polypeptide encoded by the polynucleotide of SEQ ID NO. 21, also shown in FIG. 3A.

SEQ ID NO.24 is the polypeptide encoded by the polynucleotide of SEQ ID NO. 22, also shown in FIG. 3B.

SEQ ID NO. 25 is the coding sequence of the map2 gene from *Cowdria ruminantium*.

SEQ ID NO.26 is the polypeptide encoded by the polynucleotide of SEQ ID NO. 25.

SEQ ID NO. 27 is the coding sequence of the ihworf3 gene from *Cowdria ruminantium*.

SEQ ID NO.28 is the polypeptide encoded by the polynucleotide of SEQ ID NO. 27.

SEQ ID NO. 29 is the coding sequence of the 4hworf1 gene from *Cowdria ruminantium*.

SEQ ID NO.30 is the polypeptide encoded by the polynucleotide of SEQ ID NO. 29.

SEQ ID NO. 31 is the coding sequence of the 18hworf1 gene from *Cowdria ruminantium*.

SEQ ID NO.32 is the polypeptide encoded by the polynucleotide of SEQ ID NO. 31.

SEQ ID NO. 33 is the coding sequence of the 3gdorf3 gene from *Cowdria ruminantium*.

SEQ ID NO.34 is the polypeptide encoded by the polynucleotide of SEQ ID NO. 33.

DETAILED DISCLOSURE OF THE INVENTION

In one embodiment, the subject invention concerns a novel strategy, termed nucleic acid vaccination, for eliciting an immune response protective against rickettsial disease. The subject invention also concerns novel compositions that can be employed according to this novel strategy for eliciting a protective immune response.

According to the subject invention, recombinant DNA or mRNA encoding an antigen of interest is inoculated directly into the human or animal host where an immune response is induced. Prokaryotic signal sequences maybe deleted from the nucleic acid encoding an antigen of interest. Advantageously, problems of protein purification, as can be encountered with antigen delivery using live vectors, can be virtually eliminated by employing the compositions or methods according to the subject invention. Unlike live vector delivery, the subject invention can provide a further advantage in that the DNA or RNA does not replicate in the host, but remains episomal. See, for example, Wolff, J. A., J. J. Ludike, G. Acsadi, P. Williams, A. Jani (1992) *Hum. Mol. Genet.* 1:363. A complete immune response can be obtained as recombinant antigen is synthesized intracellularly and presented to the host immune system in the context of autologous class I and class II MHC molecules.

In one embodiment, the subject invention concerns nucleic acids and compositions comprising those nucleic acids that can be effective in protecting an animal from disease or death caused by rickettsia. For example, a nucleic acid vaccine of the subject invention has been shown to be protective against *Cowdria ruminantium*, the causative agent of heartwater in domestic ruminants. Accordingly, nucleotide sequences of rickettsial genes, as described herein, can be used as nucleic acid vaccines against human and animal rickettsial diseases.

In one embodiment of the subject invention, the polynucleotide vaccines are administered in conjunction with an antigen. In a preferred embodiment, the antigen is the polypeptide which is encoded by the polynucleotide administered as the polynucleotide vaccine. As a particularly preferred embodiment, the antigen is administered as a booster subsequent to the initial administration of the polynucleotide vaccine. In another embodiment of the invention, the polynucleotide vaccine is administered in the form of a "cocktail" which contains at least two of the nucleic acid vaccines of the subject invention. The "cocktail" may be administered in conjunction with an antigen or an antigen booster as described above.

The MAP1 gene, which can be used to obtain this protection, is also present in other rickettsiae including *Anaplasma marginale, Ehrlichia canis*, and in a causative agent of human ehrlichiosis, *Ehrlichia chaffeensis* (van Vliet, A., F. Jongejan, M. van Kleef, B. van der Zeijst [1994] *Infect. Immun.* 62:1451). The MAP1 gene or a MAP1-like gene can also be found in certain Rickettsia spp. MAP1-like genes from *Ehrlichia chaffeensis* and *Ehrlichia canis* have now been cloned and sequenced. These MAP-1 homologs are also referred to herein as Variable Surface Antigen (VSA) genes.

The present invention also concerns polynucleotides encoding MAP2 or MAP2 homologs from *Ehrlichia canis* and *Ehrlichia chaffeensis*. MAP2 polynuoleotide sequences of the invention can be used as vaccine compositions and in diagnostic assays. The polynucleotides can also be used to produce the MAP2 polypeptides encoded thereby.

The subject invention further concerns the genes designated *Cowdria ruminantium* map 2, *Cowdria ruminantium* 1hworf3, *Cowdria ruminantium* 4hworf1, *Cowdria ruminantium* 18hworf1, and *Cowdria ruminantium* 3gdorf3 and the use of these genes in diagnostic and therapeutic applications. The subject invention further concerns the proteins encoded by the exemplified genes, antibodies to these proteins, and the use of such antibodies and proteins in diagnostic and therapeutic applications.

Compositions comprising the subject polynucleotides can include appropriate nucleic acid vaccine vectors (plasmids), which are commercially available (e.g., Vical, San Diego, Calif.). In addition, the compositions can include a pharmaceutically acceptable carrier, e.g., saline. The pharmaceutically acceptable carriers are well known in the art and also are commercially available. For example, such acceptable carriers are described in E. W. Martin's *Remington's Pharmaceutical Science*, Mack Publishing Company, Easton, Pa.

The subject invention also concerns polypeptides encoded by the subject polynucleotides. Specifically exemplified are the polypeptides encoded by the MAP-1 and VSA genes of *C. rumimontium*, *E. chaffeensis*, *E. canis* and the MP4 gene of *Anaplasma marginale*. Polypeptides uncoded by *E. chaffeensis* and *E. canis* MAP2 genes are also exemplified herein.

Also encompassed within the scope of the present invention are fragments and variants of the exemplified polynucleotides and polypeptides. Fragments would include, for example, portions of the exemplified sequences wherein procaryotic signal sequences have been removed. Examples of the removal of such sequences are given in Example 3. Variants include polynucleotides and/or polypeptides having base or amino acid additions, deletions and substitutions in the sequence of the subject molecule so long as those variants have substantially the same activity or, serologic reactivity as the native molecules. Also included are allelic variants of the subject polynucleotides. The polypeptides of the present invention can be used to raise antibodies that are reactive with the polypeptides disclosed herein. The polypeptides and polynucleotides can also be used as molecular weight markers.

Another aspect of the subject invention concerns antibodies reactive with MAP-1 and MAP2 polypeptides disclosed herein. Antibodies can be monoclonal or polyclonal and can be produced using standard techniques known in the art. Antibodies of the invention can be used in diagnostic and therapeutic applications.

In a specific embodiment, the subject invention concerns a DNA vaccine (e.g., VCL1010/MAP1) containing the major antigenic protein 1 gene (MAP1) driven by the human cytomegalovirus (HCMV) enhancer-promoter. In a specific example, this vaccine was injected intramuscularly into 8–10 week-old female DBA/2 mice after treating them with 50 $\mu$l/muscle of 0.5% bupivacaine 3 days previously. Up to 75% of the VCL1010/MAP1-immunized mice seroconverted and reacted with MAP1 in antigen blots. Splenocytes from immunized mice, but not from control mice immunized with VCL1010 DNA (plasmid vector, Vical, San Diego) proliferated in response to recombinant MAP1 and *C. ruminantium* antigens in in vitro lymphocyte proliferation tests. These proliferating cells from mice immunized with VCL1010/MAP1 DNA secreted IFN-gamma and IL-2 at concentrations ranging from 610 pg/ml and 152 pg/ml to 1290 pg/ml and 310 pg/ml, respectively. In experiments testing different VCL1010/MAP1 DNA vaccine dose regimens; (25–100 $\mu$g/dose, 2 or 4 immunizations), survival rates of 23% to 88% (35/92 survivors/total in all VCL1010/MAP1 immunized groups) were observed on challenge with 30LD50 of *C. ruminantium*. Survival rates of 0% to 3% (1/144 survivors/total in all control groups) were recorded for control mice immunized similarly with VCL1010 DNA or saline. Accordingly, in a specific embodiment, the subject invention concerns the discovery that the gene encoding the MAP1 protein induces protective immunity as a DNA vaccine against rickettsial disease.

The nucleic acid sequences described herein have other uses as well. For example, the nucleic acids of the subject invention can be useful as probes to identify complementary sequences within other nucleic acid molecules or genomes. Such use of probes can be applied to identify or distinguish infectious strains of organisms in diagnostic procedures or in rickettsial research where identification of particular organisms or strains is needed. As is well known in the art, probes can be made by labeling the nucleic acid sequences of interest according to accepted nucleic acid labeling procedures and techniques. A person of ordinary skill in the art would recognize that variations or fragments of the disclosed sequences which can specifically and selectively hybridize to the DNA of rickettsia can also function as a probe. It is within the ordinary skill of persons in the art, and does not require undue experimentation in view of the description provided herein, to determine whether a segment of the claimed DNA sequences is a fragment or variant which has characteristics of the full sequence, e.g., whether it specifically and selectively hybridizes or can confer protection against rickettsial infection in accordance with the subject invention. In addition, with the benefit of the subject disclosure describing the specific sequences, it is within the ordinary skill of those persons in the art to label hybridizing sequences to produce a probe.

Various degrees of stringency of hybridization can be employed. The more severe the conditions, the greater the complementarity that is required for duplex formation. Severity of conditions can be controlled by temperature, probe concentration, probe length, ionic strength, time, and the like. Preferably, hybridization is conducted under moderate to high stringency conditions by techniques well known in the art, as described, for example, in Keller, G. H., M. M. Manak (1987) *DNA Probes*, Stockton Press, New York, N.Y., pp. 169–170.

Examples of various stringency conditions are provided herein. Hybridization of immobilized DNA on Southern blots with 32P-labeled gene-specific probes can be performed by standard methods (Maniatis et al. (1982) *Molecular Cloning: A Laboratory Manual*, Cold Spring Harbor Laboratory, New York.). In general, hybridization and subsequent washes can be carried out under moderate to high stringency conditions that allow for detection of target sequences with homology to the exemplified polynucleotide sequence. For double-stranded DNA gene probes, hybridization can be carried out overnight at 20–25° C. below the melting temperature (Tm) of the DNA hybrid in 6×SSPE, 5×Denhardt's solution, 0.1% SDS, 0.1 mg/ml denatured DNA. The melting temperature is described by the following formula (Beltz et al. et al. [1983] *Methods of Enzymology*, R. Wu, L. Grossman and K. Moldave [eds.] Academic Press. New York 100:266–285).

$$Tm=81.5°\text{ C.}+16.6\text{ Log[Na+]}+0.41(\%\ G+C)-0.61(\%\text{ formamide})-600/\text{length of duplex in base pairs.}$$

Washes are typically carried out as follows:

(1) twice at room temperature for 15 minutes in 1×SSPE, 0.1% SDS (low stringency wash);

(2) once at Tm−20° C. for 15 minutes in 0.2×SSPE 0.1% SDS (moderate stringency wash).

For oligonucleotide probes, hybridization can be carried out overnight at 10–20° C. below the melting temperature (Tm) of the hybrid in 6×SSPE, 5×Denhardt's solution, 0.1% SDS, 0.1 mg/ml denatured DNA. Tm for oligonucleotide probes can be determined by the following formula:

Tm (° C.)=2(number T/A base pairs)+4(number G/C base pairs) (Suggs et al. [1981] *ICN-UCLA Symp. Dev. Biol.*

Using Purified Genes, D. D. Brown [ed.], Academic Press, New York, 23:683–693).

Washes can be carried out as follows:

(1) twice at room temperature for 15 minutes 1×SSPE, 0.1% SDS (low stringency wash;

(2) once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used:

Low: 1 or 2×SSPE, room temperature

Low: 1 or 2×SSPE, 42° C.

Moderate: 0.2×or 1×SSPE, 65° C.

High: 0.1×SSPE, 65° C.

Duplex formation and stability depend on substantial complementarity between the two strands of a hybrid and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions and deletions can be produced in a given polynucleotide sequence in many ways, and these methods are known to an ordinarily skilled artisan. Other methods may become known in the future.

It is also well known in the art that restriction enzymes can be used to obtain functional fragments of the subject DNA sequences. For example, Bal31 exonuclease can be conveniently used for time-controlled limited digestion of DNA (commonly referred to as "erase-a-base" procedures). See, for example, Maniatis et al. (1982) *Molecular Cloning: A Laboratory Manual*, Cold Spring Harbor Laboratory, New York; Wei et al. (1983) *J. Biol. Chem.* 258:13006–13512.

In addition, the nucleic acid sequences of the subject invention can be used as molecular weight markers in nucleic acid analysis procedures.

Following are examples which illustrate procedures for practicing the invention. These examples should not be construed as limiting. All percentages are by weight and all solvent mixture proportions are by volume unless otherwise noted.

EXAMPLE 1

A nucleic acid vaccine construct was tested in animals for its ability to protect against death caused by infection with the rickettsia *Cowdria ruminantium*. The vaccine construct tested was the MAP1 gene of *C. ruminantium* inserted into plasmid VCL1010 (Vical, San Diego) under control of the human cytomegalovirus promoter-enhancer and intron A. In this study, seven groups containing 10 mice each were injected twice at 2-week intervals with either 100, 75, 50, or 25 µg VCL1010/MAP1 DNA (V/M in Table 1 below), or 100, 50 µg VCL1010 DNA (V in Table 1) or saline (Sal.), respectively. Two weeks after the last injections, 8 mice/group were challenged with 30LD50 of *C. ruminantium* and clinical symptoms and survival monitored. The remaining 2 mice/group were not challenged and were used for lymphocyte proliferation tests and cytokine measurements. The results of the study are summarized in Table 1, below:

TABLE 1

|  | 100 µg V/M | 75 µg V/M | 50 µg V/M | 25 µg V/M | 100 µg V | 50 µg V | Sal. |
|---|---|---|---|---|---|---|---|
| Survived | 5 | 7 | 5 | 3 | 0 | 0 | 0 |
| Died | 3 | 1 | 3 | 5 | 8 | 8 | 8 |

The VCL1010/MAP1 nucleic acid vaccine increased survival on challenge in all groups, with a total of 20/30 mice surviving compared to 0/24 in the control groups.

This study was repeated with another 6 groups, each containing 33 mice (a total of 198 mice). Three groups received 75 µg VCL1010/MAP1 DNA or VCL1010 DNA or saline (4 injections in all cases). Two weeks after the last injection, 30 mice/group were challenged with 30LD50 of *C. ruminantium* and 3 mice/group were sacrificed for lymphocyte proliferation tests and cytokine measurements. The results of this study are summarized in Table 2, below:

TABLE 2

|  | V/M 2 inj. | V 2 inj. | Sal. 2 inj. | V/M 4 inj. | V 4 inj. | Sal. 4 inj. |
|---|---|---|---|---|---|---|
| Survived | 7 | 0 | 0 | 8 | 0 | 1 |
| Died* | 23 | 30 | 30 | 22 | 30 | 29 |

*In mice that died in both V/M groups, there was an increase in mean survival time of approximately 4 days compared to the controls (p < 0.05).

Again, as summarized in Table 2, the VCL1010/MAP1 DNA vaccine increased the numbers of mice surviving in both immunized groups, although there was no apparent benefit of 2 additional injections. In these two experiments there were a cumulative total of 35/92 (38%) surviving mice in groups receiving the VCL1010/MAP1 DNA vaccine compared to 1/144 (0.7%) surviving mice in the control groups. In both immunization and challenge trials described above, splenocytes from VCL1010/MAP1 immunized mice, but not from control mice, specifically proliferated to recombinant MAP1 protein and to *C. ruminantium* in lymphocyte proliferation tests. These proliferating splenocytes secreted IL-2 and gamma-interferon at concentrations up to 310 and 1290 pg/ml respectively. These data show that protection against rickettsial infections can be achieved with a DNA vaccine. In addition, these experiments show MAP1-related proteins as vaccine targets.

EXAMPLE 2

Cloning and Sequence Analysis of MAP1 Homologue Genes of *E. chaffeensis* and *E. canis*

Genes homologous to the major surface protein of *C. ruminantium* MAP1 were cloned from *E. chaffeensis* and *E. canis* by using PCR cloning strategies. The cloned segments represent a 4.6 kb genomic locus of *E. chaffeensis* and a 1.6 kb locus of *E. canis*. DNA sequence generated from these clones was assembled and is presented along with the deduced amino acid sequence in FIGS. 2A–2B (SEQ ID NOs. 7–11 and 14–18) and FIG. 2C (SEQ ID NOs. 12–13 and 19–20). Significant features of the DNA include five very similar but nonidentical open reading frames (ORFs) for *E. chaffeensis* and two very similar, nonidentical ORFs for the *E. canis* cloned locus. The ORFs for both Ehrlichia spp. are separated by noncoding sequences ranging from 264 to 310 base pairs. The noncoding sequences have a higher A+T content (71.6% for *E. chaffeensis* and 76.1% for *E. canis*) than do the coding sequences (63.5% for *E.* chaffeensis and 68.0% for *E. canis*). A G-rich region −200 bases upstream from the initiation codon, sigma-70-like promoter sequences, putative ribosome binding sites (RBS), termination codons, and palindromic sequences near the termination codons are found in each of the *E. chaffeensis* noncoding sequences. The *E. canis* noncoding sequence has the same feature except for the G-rich region (FIG. 2C; SEQ ID NOs. 12–13 and 19–20).

Sequence comparisons of the ORFs at the nucleotide and translated amino acid levels revealed a high degree of similarity between them. The similarity spanned the entire coding sequences, except in three regions where notable sequence variations were observed including some deletions/insertions(Variable Regions I, II and III). Despite the similarities, no two ORFs are identical. The cloned ORF 2, 3 and 4 of *E. chaffeensis* have complete coding sequences. The ORF1 is a partial gene having only 143 amino acids at the C-terminus whereas the ORF5 is nearly complete but lacks 5–7 amino acids and a termination codon. The cloned ORF2 of *E. canis* also is a partial gene lacking a part of the C-terminal sequence. The overall similarity between different ORFs at the amino acid level is 56.0% to 85.4% for *E. chaffeensis*, whereas for *E. canis* it is 53.3%. The similarity of *E. chaffeensis* ORFs to the MAP1 coding sequences reported for *C. ruminantium* isolates ranged from 55.5% to 66.7%, while for *E. canis* to *C. ruminantium* it is 48.5% to 54.2%. Due to their high degree of similarity to MAP1 surface antigen genes of *C. ruminantium* and since they are nonidentical to each other, the *E. chaffeensis* and *E. canis* ORFs are referred to herein as putative Variable Surface Antigen (VSA) genes. The apparent molecular masses of the predicted mature proteins of *E. chaffeensis* were 28.75 kDa for VSA2, 27.78 for VSA3, and 27.95 for VSA4, while *E. canis* VSA1 was slightly higher at 29.03 kDa. The first 25 amino acids in each VSA coding sequence were eliminated when calculating the protein size since they markedly resembled the signal sequence of *C. ruminantium* MAP1 and presumably would be absent from the mature protein.

The amino acid sequence derived from the cloned *E. chaffeensis* MAP1-like gene, and alignment with the corresponding genes of *C. ruminantium* and *A. marginale* is shown in FIG. 1.

EXAMPLE 3

A further aspect of the subject invention are five additional genes which give protection when formatted as DNA vaccines. These genes are *Cowdria ruminantium* map 2, *Cowdria ruminantium* 1hworf3, *Cowdria ruminantium* 4hworf1, *Cowdria ruminantium* 18hworf1, and *Cowdria ruminantium* 3gdorf3. The DNA and translated amino acid sequences of these five genes are shown in SEQ ID NOS. 25–34.

There is published information showing that gene homologs of all five genes are present in other bacteria. For example, a homolog of map2 is present in *Anaplasma marginale*, a homolog of 1hworf3 is present in *Brucella abortus*, homologs of 4hworf1 are present in *Pseudomonas aeruginosa* and *Coxiella burnetii*, and homologs of 18hworf1 are present in *Coxiella burnetii* and *Rickettsia prowazekii*. This can be revealed by a search of DNA and protein databases with standard search algorithms such as "Blast". Based on the protective ability of these genes against *Cowdria ruminantium* and their presence in other bacterial pathogens, the subject invention further concerns the use of these genes, their gene products, and the genes and gene products of the homologs as vaccines against bacteria. This includes their use as DNA or nucleic acid vaccines or when formulated in vaccines employing other methods of delivery, e.g., recombinant proteins or synthetic peptides in adjuvants, recombinant live vector delivery systems such as vaccinia (or other live viruses) or Salmonella (or other live bacteria). These methods of delivery are standard to those familiar with the field. This also includes vaccines against heartwater disease, vaccines against rickettsial diseases in general and vaccines against other bacteria containing homologs of these genes.

Table 3 shows the protective ability of the 5 genes against death from *Cowdria ruminantium* challenge in mice. Genes were inserted into VR1012 according to the manufacturers instructions (Vical, San Diego) and challenge studies were conducted as described in Example 1. N-terminal sequences which putatively encoded prokaryotic signal peptides were deleted because of the potential for their affects on expression and and immune responses in eukaryotic expression systems or challenged animals. The inserts were as follows: map2, SEQ ID NO. 25, beginning at base 46; 18hworf1, SEQ ID NO. 31, beginning at base 67; 3gdorf3, SEQ ID NO. 33, beginning at base 79; 1hworf3, SEQ ID NO. 27, beginning at base 76; and 4hworf1, SEQ ID NO. 29, beginning at base 58.

TABLE 3

| DNA Construct | MWT Size | Survival Rate | | P value |
| --- | --- | --- | --- | --- |
| | | Vaccinated | Control | |
| TMMAP 2 | 21 kd | 9/28* 32% | 0/29 0% | 0.004 |
| MB18HWORF1 | 28 kd | 10/30* 33% | 1/27 4% | 0.021 |
| AM3GDORF3 | 16 kd | 7/26 27% | 1/27 4% | 0.060 |
| TM1HWORF3 | 36 kd | 8/29 28% | 2/30 7% | 0.093 |
| TM4HWORF1 | 19 kd | 10/30* 33% | 2/30 7% | 0.054 |

Control-VR1012 DNA vector plasmid only
*Statistically significant difference (Fisher's Exact test)

It should be understood that the examples and embodiments described herein are for illustrative purposes only and that various modifications or changes in light thereof will be suggested to persons skilled in the art and are to be included within the spirit and purview of this application and the scope of the appended claims.

SEQUENCE LISTING

<160> NUMBER OF SEQ ID NOS: 34

<210> SEQ ID NO 1
<211> LENGTH: 864
<212> TYPE: DNA
<213> ORGANISM: Cowdria ruminantium -continued

```
<220> FEATURE:
<221> NAME/KEY: CDS
<222> LOCATION: (1)..(861)

<400> SEQUENCE: 1 atg aat tgc aag aaa att ttt atc aca agt aca cta ata tca tta gtg     48
Met Asn Cys Lys Lys Ile Phe Ile Thr Ser Thr Leu Ile Ser Leu Val
 1               5                  10                  15 tca ttt tta cct ggt gtg tcc ttt tct gat gta ata cag gaa gac agc     96
Ser Phe Leu Pro Gly Val Ser Phe Ser Asp Val Ile Gln Glu Asp Ser
             20                  25                  30 aac cca gca ggc agt gtt tac att agc gca aaa tac atg cca act gca    144
Asn Pro Ala Gly Ser Val Tyr Ile Ser Ala Lys Tyr Met Pro Thr Ala
         35                  40                  45 tca cat ttt ggt aaa atg tca atc aaa gaa gat tca aaa aat act caa    192
Ser His Phe Gly Lys Met Ser Ile Lys Glu Asp Ser Lys Asn Thr Gln
     50                  55                  60 acg gta ttt ggt cta aaa aaa gat tgg gat ggc gtt aaa aca cca tca    240
Thr Val Phe Gly Leu Lys Lys Asp Trp Asp Gly Val Lys Thr Pro Ser
 65                  70                  75                  80 gat tct agc aat act aat tct aca att ttt act gaa aaa gac tat tct    288
Asp Ser Ser Asn Thr Asn Ser Thr Ile Phe Thr Glu Lys Asp Tyr Ser
                 85                  90                  95 ttc aga tat gaa aac aat ccg ttt tta ggt ttc gct gga gca att ggg    336
Phe Arg Tyr Glu Asn Asn Pro Phe Leu Gly Phe Ala Gly Ala Ile Gly
            100                 105                 110 tac tca atg aat gga cca aga ata gag ttc gaa gta tcc tat gaa act    384
Tyr Ser Met Asn Gly Pro Arg Ile Glu Phe Glu Val Ser Tyr Glu Thr
        115                 120                 125 ttt gat gta aaa aac cta ggt ggc aac tat aaa aac aac gca cac atg    432
Phe Asp Val Lys Asn Leu Gly Gly Asn Tyr Lys Asn Asn Ala His Met
130                 135                 140 tac tgt gct tta gat aca gca gca caa aat agc act aat ggc gca gga    480
Tyr Cys Ala Leu Asp Thr Ala Ala Gln Asn Ser Thr Asn Gly Ala Gly
145                 150                 155                 160 tta act aca tct gtt atg gta aaa aac gaa aat tta aca aat ata tca    528
Leu Thr Thr Ser Val Met Val Lys Asn Glu Asn Leu Thr Asn Ile Ser
                165                 170                 175 tta atg tta aat gcg tgt tat gat atc atg ctt gat gga ata cca gtt    576
Leu Met Leu Asn Ala Cys Tyr Asp Ile Met Leu Asp Gly Ile Pro Val
            180                 185                 190 tct cca tat gta tgt gca ggt att ggc act gac tta gtg tca gta att    624
Ser Pro Tyr Val Cys Ala Gly Ile Gly Thr Asp Leu Val Ser Val Ile
        195                 200                 205 aat gct aca aat cct aaa tta tct tat caa gga aag cta ggc ata agt    672
Asn Ala Thr Asn Pro Lys Leu Ser Tyr Gln Gly Lys Leu Gly Ile Ser
210                 215                 220 tac tca atc aat tct gaa gct tct atc ttt atc ggt gga cat ttc cat    720
Tyr Ser Ile Asn Ser Glu Ala Ser Ile Phe Ile Gly Gly His Phe His
225                 230                 235                 240 aga gtt ata ggt aat gaa ttt aaa gat att gct acc tta aaa ata ttt    768
Arg Val Ile Gly Asn Glu Phe Lys Asp Ile Ala Thr Leu Lys Ile Phe
                245                 250                 255 act tca aaa aca gga ata tct aat cct ggc ttt gca tca gca aca ctt    816
Thr Ser Lys Thr Gly Ile Ser Asn Pro Gly Phe Ala Ser Ala Thr Leu
            260                 265                 270 gat gtt tgt cac ttt ggt ata gaa att gga gga agg ttt gta ttt taa    864
Asp Val Cys His Phe Gly Ile Glu Ile Gly Gly Arg Phe Val Phe
        275                 280                 285
```

```
<210> SEQ ID NO 2
<211> LENGTH: 287
<212> TYPE: PRT
<213> ORGANISM: Cowdria ruminantium

<400> SEQUENCE: 2

Met Asn Cys Lys Lys Ile Phe Ile Thr Ser Thr Leu Ile Ser Leu Val
 1               5                   10                  15

Ser Phe Leu Pro Gly Val Ser Phe Ser Asp Val Ile Gln Glu Asp Ser
             20                  25                  30

Asn Pro Ala Gly Ser Val Tyr Ile Ser Ala Lys Tyr Met Pro Thr Ala
         35                  40                  45

Ser His Phe Gly Lys Met Ser Ile Lys Glu Asp Ser Lys Asn Thr Gln
     50                  55                  60

Thr Val Phe Gly Leu Lys Lys Asp Trp Asp Gly Val Lys Thr Pro Ser
65                  70                  75                  80

Asp Ser Ser Asn Thr Asn Ser Thr Ile Phe Thr Glu Lys Asp Tyr Ser
                 85                  90                  95

Phe Arg Tyr Glu Asn Asn Pro Phe Leu Gly Phe Ala Gly Ala Ile Gly
            100                 105                 110

Tyr Ser Met Asn Gly Pro Arg Ile Glu Phe Glu Val Ser Tyr Glu Thr
        115                 120                 125

Phe Asp Val Lys Asn Leu Gly Gly Asn Tyr Lys Asn Asn Ala His Met
130                 135                 140

Tyr Cys Ala Leu Asp Thr Ala Ala Gln Asn Ser Thr Asn Gly Ala Gly
145                 150                 155                 160

Leu Thr Thr Ser Val Met Val Lys Asn Glu Asn Leu Thr Asn Ile Ser
                165                 170                 175

Leu Met Leu Asn Ala Cys Tyr Asp Ile Met Leu Asp Gly Ile Pro Val
            180                 185                 190

Ser Pro Tyr Val Cys Ala Gly Ile Gly Thr Asp Leu Val Ser Val Ile
        195                 200                 205

Asn Ala Thr Asn Pro Lys Leu Ser Tyr Gln Gly Lys Leu Gly Ile Ser
    210                 215                 220

Tyr Ser Ile Asn Ser Glu Ala Ser Ile Phe Ile Gly Gly His Phe His
225                 230                 235                 240

Arg Val Ile Gly Asn Glu Phe Lys Asp Ile Ala Thr Leu Lys Ile Phe
                245                 250                 255

Thr Ser Lys Thr Gly Ile Ser Asn Pro Gly Phe Ala Ser Ala Thr Leu
            260                 265                 270

Asp Val Cys His Phe Gly Ile Glu Ile Gly Gly Arg Phe Val Phe
        275                 280                 285

<210> SEQ ID NO 3
<211> LENGTH: 842
<212> TYPE: DNA
<213> ORGANISM: Ehrlichia chaffeensis
<220> FEATURE:
<221> NAME/KEY: CDS
<222> LOCATION: (1)..(840)

<400> SEQUENCE: 3 atg aat tac aaa aaa agt ttc ata aca gcg att gat atc att aat atc       48
Met Asn Tyr Lys Lys Ser Phe Ile Thr Ala Ile Asp Ile Ile Asn Ile
 1               5                   10                  15 ctt ctc tta cct gga gta tca ttt tcc gac cca agg cag gta gtg gtc      96
Leu Leu Leu Pro Gly Val Ser Phe Ser Asp Pro Arg Gln Val Val Val
             20                  25                  30
```

```
att aac ggt aat ttc tac atc agt gga aaa tac gat gcc aag gct tcg      144
Ile Asn Gly Asn Phe Tyr Ile Ser Gly Lys Tyr Asp Ala Lys Ala Ser
        35                  40                  45 cat ttt gga gta ttc tct gct aag gaa gaa aga aat aca aca gtt gga      192
His Phe Gly Val Phe Ser Ala Lys Glu Glu Arg Asn Thr Thr Val Gly
 50                  55                  60 gtg ttt gga ctg aag caa aat tgg gac gga agc gca ata tcc aac tcc      240
Val Phe Gly Leu Lys Gln Asn Trp Asp Gly Ser Ala Ile Ser Asn Ser
 65                  70                  75                  80 tcc cca aac gat gta ttc act gtc tca aat tat tca ttt aaa tat gaa      288
Ser Pro Asn Asp Val Phe Thr Val Ser Asn Tyr Ser Phe Lys Tyr Glu
                 85                  90                  95 aac aac ccg ttt tta ggt ttt gca gga gct att ggt tac tca atg gat      336
Asn Asn Pro Phe Leu Gly Phe Ala Gly Ala Ile Gly Tyr Ser Met Asp
            100                 105                 110 ggt cca aga ata gag ctt gaa gta tct tat gaa aca ttt gat gta aaa      384
Gly Pro Arg Ile Glu Leu Glu Val Ser Tyr Glu Thr Phe Asp Val Lys
        115                 120                 125 aat caa ggt aac aat tat aag aat gaa gca cat aga tat tgt gct cta      432
Asn Gln Gly Asn Asn Tyr Lys Asn Glu Ala His Arg Tyr Cys Ala Leu
    130                 135                 140 tcc cat aac tca gca gca gac atg agt agt gca agt aat aat ttt gtc      480
Ser His Asn Ser Ala Ala Asp Met Ser Ser Ala Ser Asn Asn Phe Val
145                 150                 155                 160 ttt cta aaa aat gaa gga tta ctt gac ata tca ttt atg ctg aac gca      528
Phe Leu Lys Asn Glu Gly Leu Leu Asp Ile Ser Phe Met Leu Asn Ala
                165                 170                 175 tgc tat gac gta gta ggc gaa ggc ata cct ttt tct cct tat ata tgc      576
Cys Tyr Asp Val Val Gly Glu Gly Ile Pro Phe Ser Pro Tyr Ile Cys
            180                 185                 190 gca ggt atc ggt act gat tta gta tcc atg ttt gaa gct aca aat cct      624
Ala Gly Ile Gly Thr Asp Leu Val Ser Met Phe Glu Ala Thr Asn Pro
        195                 200                 205 aaa att tct tac caa gga aag tta ggt tta agc tac tct ata agc cca      672
Lys Ile Ser Tyr Gln Gly Lys Leu Gly Leu Ser Tyr Ser Ile Ser Pro
    210                 215                 220 gaa gct tct gtg ttt att ggt ggg cac ttt cat aag gta ata ggg aac      720
Glu Ala Ser Val Phe Ile Gly Gly His Phe His Lys Val Ile Gly Asn
225                 230                 235                 240 gaa ttt aga gat att cct act ata ata cct act gga tca aca ctt gca      768
Glu Phe Arg Asp Ile Pro Thr Ile Ile Pro Thr Gly Ser Thr Leu Ala
                245                 250                 255 gga aaa gga aac tac cct gca ata gta ata ctg gat gta tgc cac ttt      816
Gly Lys Gly Asn Tyr Pro Ala Ile Val Ile Leu Asp Val Cys His Phe
            260                 265                 270 gga ata gaa atg gga gga agg ttt aa                                    842
Gly Ile Glu Met Gly Gly Arg Phe
        275                 280

<210> SEQ ID NO 4
<211> LENGTH: 280
<212> TYPE: PRT
<213> ORGANISM: Ehrlichia chaffeensis
<400> SEQUENCE: 4

Met Asn Tyr Lys Lys Ser Phe Ile Thr Ala Ile Asp Ile Ile Asn Ile
 1               5                  10                  15

Leu Leu Leu Pro Gly Val Ser Phe Ser Asp Pro Arg Gln Val Val Val
                20                  25                  30
Ile Asn Gly Asn Phe Tyr Ile Ser Gly Lys Tyr Asp Ala Lys Ala Ser
        35                  40                  45
```

```
His Phe Gly Val Phe Ser Ala Lys Glu Glu Arg Asn Thr Thr Val Gly
    50                  55                  60

Val Phe Gly Leu Lys Gln Asn Trp Asp Gly Ser Ala Ile Ser Asn Ser
65                  70                  75                  80

Ser Pro Asn Asp Val Phe Thr Val Ser Asn Tyr Ser Phe Lys Tyr Glu
                85                  90                  95

Asn Asn Pro Phe Leu Gly Phe Ala Gly Ala Ile Gly Tyr Ser Met Asp
            100                 105                 110

Gly Pro Arg Ile Glu Leu Glu Val Ser Tyr Glu Thr Phe Asp Val Lys
        115                 120                 125

Asn Gln Gly Asn Asn Tyr Lys Asn Glu Ala His Arg Tyr Cys Ala Leu
    130                 135                 140

Ser His Asn Ser Ala Ala Asp Met Ser Ser Ala Ser Asn Asn Phe Val
145                 150                 155                 160

Phe Leu Lys Asn Glu Gly Leu Leu Asp Ile Ser Phe Met Leu Asn Ala
                165                 170                 175

Cys Tyr Asp Val Val Gly Glu Gly Ile Pro Phe Ser Pro Tyr Ile Cys
            180                 185                 190

Ala Gly Ile Gly Thr Asp Leu Val Ser Met Phe Glu Ala Thr Asn Pro
        195                 200                 205

Lys Ile Ser Tyr Gln Gly Lys Leu Gly Leu Ser Tyr Ser Ile Ser Pro
    210                 215                 220

Glu Ala Ser Val Phe Ile Gly Gly His Phe His Lys Val Ile Gly Asn
225                 230                 235                 240

Glu Phe Arg Asp Ile Pro Thr Ile Ile Pro Thr Gly Ser Thr Leu Ala
                245                 250                 255

Gly Lys Gly Asn Tyr Pro Ala Ile Val Ile Leu Asp Val Cys His Phe
            260                 265                 270

Gly Ile Glu Met Gly Gly Arg Phe
        275                 280

<210> SEQ ID NO 5
<211> LENGTH: 849
<212> TYPE: DNA
<213> ORGANISM: Anaplasma marginale
<220> FEATURE:
<221> NAME/KEY: CDS
<222> LOCATION: (1)..(846)

<400> SEQUENCE: 5 atg aat tac aga gaa ttg ttt aca ggg ggc ctg tca gca gcc aca gtc     48
Met Asn Tyr Arg Glu Leu Phe Thr Gly Gly Leu Ser Ala Ala Thr Val
1               5                   10                  15 tgc gcc tgc tcc cta ctt gtt agt ggg gcc gta gtg gca tct ccc atg     96
Cys Ala Cys Ser Leu Leu Val Ser Gly Ala Val Val Ala Ser Pro Met
            20                  25                  30 agt cac gaa gtg gct tct gaa ggg gga gta atg gga ggt agc ttt tac    144
Ser His Glu Val Ala Ser Glu Gly Gly Val Met Gly Gly Ser Phe Tyr
        35                  40                  45 gtg ggt gcg gcc tac agc cca gca ttt cct tct gtt acc tcg ttc gac    192
Val Gly Ala Ala Tyr Ser Pro Ala Phe Pro Ser Val Thr Ser Phe Asp
50                  55                  60 atg cgt gag tca agc aaa gag acc tca tac gtt aga ggc tat gac aag    240
Met Arg Glu Ser Ser Lys Glu Thr Ser Tyr Val Arg Gly Tyr Asp Lys
65                  70                  75                  80 agc att gca acg att gat gtg agt gtg cca gca aac ttt tcc aaa tct    288
Ser Ile Ala Thr Ile Asp Val Ser Val Pro Ala Asn Phe Ser Lys Ser
```

-continued

```
                85                  90                  95
ggc tac act ttt gcc ttc tct aaa aac tta atc acg tct ttc gac ggc    336
Gly Tyr Thr Phe Ala Phe Ser Lys Asn Leu Ile Thr Ser Phe Asp Gly
            100                 105                 110 gct gtg gga tat tct ctg gga gga gcc aga gtg gaa ttg gaa gcg agc    384
Ala Val Gly Tyr Ser Leu Gly Gly Ala Arg Val Glu Leu Glu Ala Ser
        115                 120                 125 tac aga agg ttt gct act ttg gcg gac ggg cag tac gca aaa agt ggt    432
Tyr Arg Arg Phe Ala Thr Leu Ala Asp Gly Gln Tyr Ala Lys Ser Gly
    130                 135                 140 gcg gaa tct ctg gca gct att acc cgc gac gct aac att act gag acc    480
Ala Glu Ser Leu Ala Ala Ile Thr Arg Asp Ala Asn Ile Thr Glu Thr
145                 150                 155                 160 aat tac ttc gta gtc aaa att gat gaa atc aca aac acc tca gtc atg    528
Asn Tyr Phe Val Val Lys Ile Asp Glu Ile Thr Asn Thr Ser Val Met
                165                 170                 175 tta aat ggc tgc tat gac gtg ctg cac aca gat tta cct gtg tcc ccg    576
Leu Asn Gly Cys Tyr Asp Val Leu His Thr Asp Leu Pro Val Ser Pro
            180                 185                 190 tat gta tgt gcc ggg ata ggc gca agc ttt gtt gac atc tct aag caa    624
Tyr Val Cys Ala Gly Ile Gly Ala Ser Phe Val Asp Ile Ser Lys Gln
        195                 200                 205 gta acc aca aag ctg gcc tac agg ggc aag gtt ggg att agc tac cag    672
Val Thr Thr Lys Leu Ala Tyr Arg Gly Lys Val Gly Ile Ser Tyr Gln
    210                 215                 220 ttt act ccg gaa ata tcc ttg gtg gca ggt ggg ttc tac cac ggg cta    720
Phe Thr Pro Glu Ile Ser Leu Val Ala Gly Gly Phe Tyr His Gly Leu
225                 230                 235                 240 ttt gat gag tct tac aag gac att ccc gca cac aac agt gta aag ttc    768
Phe Asp Glu Ser Tyr Lys Asp Ile Pro Ala His Asn Ser Val Lys Phe
                245                 250                 255 tct gga gaa gca aaa gcc tca gtc aaa gcg cat att gct gac tac ggc    816
Ser Gly Glu Ala Lys Ala Ser Val Lys Ala His Ile Ala Asp Tyr Gly
            260                 265                 270 ttt aac ctt gga gca aga ttc ctg ttc agc taa                        849
Phe Asn Leu Gly Ala Arg Phe Leu Phe Ser
        275                 280
```

<210> SEQ ID NO 6
<211> LENGTH: 282
<212> TYPE: PRT
<213> ORGANISM: Anaplasma marginale
<400> SEQUENCE: 6

```
Met Asn Tyr Arg Glu Leu Phe Thr Gly Gly Leu Ser Ala Ala Thr Val
  1               5                  10                  15

Cys Ala Cys Ser Leu Leu Val Ser Gly Ala Val Ala Ser Pro Met
                 20                  25                  30

Ser His Glu Val Ala Ser Glu Gly Gly Val Met Gly Gly Ser Phe Tyr
             35                  40                  45

Val Gly Ala Ala Tyr Ser Pro Ala Phe Pro Ser Val Thr Ser Phe Asp
         50                  55                  60

Met Arg Glu Ser Ser Lys Glu Thr Ser Tyr Val Arg Gly Tyr Asp Lys
 65                  70                  75                  80

Ser Ile Ala Thr Ile Asp Val Ser Val Pro Ala Asn Phe Ser Lys Ser
                 85                  90                  95

Gly Tyr Thr Phe Ala Phe Ser Lys Asn Leu Ile Thr Ser Phe Asp Gly
            100                 105                 110

Ala Val Gly Tyr Ser Leu Gly Gly Ala Arg Val Glu Leu Glu Ala Ser
```

-continued

```
        115                 120                 125
Tyr Arg Arg Phe Ala Thr Leu Ala Asp Gly Gln Tyr Ala Lys Ser Gly
    130                 135                 140

Ala Glu Ser Leu Ala Ala Ile Thr Arg Asp Ala Asn Ile Thr Glu Thr
145                 150                 155                 160
Asn Tyr Phe Val Val Lys Ile Asp Glu Ile Thr Asn Thr Ser Val Met
                165                 170                 175
Leu Asn Gly Cys Tyr Asp Val Leu His Thr Asp Leu Pro Val Ser Pro
            180                 185                 190

Tyr Val Cys Ala Gly Ile Gly Ala Ser Phe Val Asp Ile Ser Lys Gln
        195                 200                 205

Val Thr Thr Lys Leu Ala Tyr Arg Gly Lys Val Gly Ile Ser Tyr Gln
    210                 215                 220

Phe Thr Pro Glu Ile Ser Leu Val Ala Gly Gly Phe Tyr His Gly Leu
225                 230                 235                 240
Phe Asp Glu Ser Tyr Lys Asp Ile Pro Ala His Asn Ser Val Lys Phe
                245                 250                 255
Ser Gly Glu Ala Lys Ala Ser Val Lys Ala His Ile Ala Asp Tyr Gly
            260                 265                 270

Phe Asn Leu Gly Ala Arg Phe Leu Phe Ser
        275                 280

<210> SEQ ID NO 7
<211> LENGTH: 132
<212> TYPE: DNA
<213> ORGANISM: Ehrlichia chaffeensis

<400> SEQUENCE: 7
ggaatgaatt cagggacatt tctactctta aagcgtttgc tacaccatca tctgcagcta      60
ctccagactt agcaacagta acactgagtg tgtgtcactt tggagtagaa cttggaggaa     120
gatttaactt ct                                                         132

<210> SEQ ID NO 8
<211> LENGTH: 861
<212> TYPE: DNA
<213> ORGANISM: Ehrlichia chaffeensis
<400> SEQUENCE: 8
atatgaactg cgaaaaattt tttataacaa ctgcattaac attactaatg tccttcttac      60
ctggaatatc actttctgat ccagtacagg atgacaacat tagtggtaat ttctacatca     120
gtggaaagta tatgccaagc gcttcgcatt ttggagtttt ttctgccaag gaagaaagaa     180
atacaacagt tggagtattt ggaatagagc aagattggga tagatgtgta atatctagaa     240
ccactttaag cgatatattc accgttccaa attattcatt taagtatgaa aataatctat     300
tttcaggatt tgcaggagct attggctact caatggatgg cccaagaata gagcttgaag     360
tatcttatga agcattcgat gttaaaaatc aaggtaacaa ttataagaac gaagcacata     420
gatattatgc tctgtcccat cttctcggca cagagacaca gatagatggt gcaggcagtg     480
cgtctgtctt tctaataaat gaaggactac ttgataaatc atttatgctg aacgcatgtt     540
atgatgtaat aagtgaaggc ataccttttt ctccttatat atgtgcaggt attggtattg     600
atttagtatc catgtttgaa gctataaatc ctaaaatttc ttatcaagga aaattaggct     660
taagttaccc tataagccca gaagcttctg tgtttattgg tggacatttt cataaggtga     720
taggaaacga atttagagat attcctacta tgatacctag tgaatcagcg cttgcaggaa     780
```

-continued

| aaggaaacta ccctgcaata gtaacactgg acgtgttcta ctttggcata gaacttggag | 840 |
| gaaggtttaa cttccaactt t | 861 |

<210> SEQ ID NO 9
<211> LENGTH: 837
<212> TYPE: DNA
<213> ORGANISM: Ehrlichia chaffeensis
<400> SEQUENCE: 9

| atatgaattg caaaaaattt tttataacaa ctgcattagt atcactaatg tcctttctac | 60 |
| ctggaatatc attttctgat ccagtgcaag gtgacaatat tagtggtaat ttctatgtta | 120 |
| gtggcaagta tatgccaagt gcttcgcatt ttggcatgtt ttctgccaaa gaagaaaaaa | 180 |
| atcctactgt tgcattgtat ggcttaaaac aagattggga agggattagc tcatcaagtc | 240 |
| acaatgataa tcatttcaat aacaaggggt attcatttaa atatgaaaat aacccatttt | 300 |
| tagggtttgc aggagctatt ggttattcaa tgggtggtcc aagagtagag tttgaagtgt | 360 |
| cctatgaaac atttgacgtt aaaaatcagg gtaataacta taaaaatgat gctcacagat | 420 |
| actgtgcttt aggtcaacaa gacaacagcg gaatacctaa aactagtaaa tacgtactgt | 480 |
| taaaaagcga aggattgctt gacatatcat ttatgctaaa tgcatgctat gatataataa | 540 |
| acgagagcat accttttgtct ccttacatat gtgcaggtgt tggtactgat ttaatatcca | 600 |
| tgtttgaagc tacaaatcct aaaatttctt accaagggaa gttaggtcta agttactcta | 660 |
| taaacccaga agcttctgta tttattggtg gacattttca taggtgata ggaaacgaat | 720 |
| ttagggacat tcctactctg aaagcatttg ttacgtcatc agctactcca gatctagcaa | 780 |
| tagtaacact aagtgtatgt cattttggaa tagaacttgg aggaaggttt aacttct | 837 |

<210> SEQ ID NO 10
<211> LENGTH: 843
<212> TYPE: DNA
<213> ORGANISM: Ehrlichia chaffeensis
<400> SEQUENCE: 10

| atatgaattg caaaaaattt tttataacaa ctacattagt atcgctaatg tccttcttac | 60 |
| ctggaatatc attttctgat gcagtacaga acgacaatgt tggtggtaat ttctatatca | 120 |
| gtgggaaata tgtaccaagt gtttcacatt ttggcgtatt ctctgctaaa caggaaagaa | 180 |
| atacaacaat cggagtattt ggattaaagc aagattggga tggcagcaca atatctaaaa | 240 |
| attctccaga aaatacattt aacgttccaa attattcatt taaatatgaa ataatccat | 300 |
| ttctaggttt tgcaggagct gttggttatt taatgaatgg tccaagaata gagttagaaa | 360 |
| tgtcctatga aacatttgat gtgaaaaacc agggtaataa ctataagaac gatgctcaca | 420 |
| aatattatgc tttaacccat aacagtgggg gaaagctaag caatgcaggt gataagtttg | 480 |
| ttttctaaa aaatgaagga ctacttgata tatcacttat gttgaatgca tgctatgatg | 540 |
| taataagtga aggaatacct ttctctcctt acatatgtgc aggtgttggt actgatttaa | 600 |
| tatccatgtt tgaagctata aaccctaaaa tttcttatca aggaaagtta ggtttgagtt | 660 |
| actccataag cccagaagct tctgttttgt ttggtggaca ttttcataag gtgataggga | 720 |
| atgaattcag agatattcct gctatgatac ccagtacctc aactctcaca ggtaatcact | 780 |
| ttactatagt aacactaagt gtatgccact ttggagtgga acttggagga aggtttaact | 840 |
| ttt | 843 |

<210> SEQ ID NO 11
<211> LENGTH: 830

-continued

```
<212> TYPE: DNA
<213> ORGANISM: Ehrlichia chaffeensis
<400> SEQUENCE: 11
atatgaatta caaaaaagtt ttcataacaa gtgcattgat atcattaata tcttctctac     60
ctggagtatc attttccgac ccagcaggta gtggtattaa cggtaatttc tacatcagtg    120
gaaaatacat gccaagtgct tcgcattttg gagtattctc tgctaaggaa gaaagaaata    180
caacagttgg agtgtttgga ctgaagcaaa attgggacgg aagcgcaata tccaactcct    240
ccccaaacga tgtattcact gtctcaaatt attcatttaa atatgaaaac aacccgtttt    300
taggttttgc aggagctatt ggttactcaa tggatggtcc aagaatagag cttgaagtat    360
cttatgaaac atttgatgta aaaaatcaag gtaacaatta taagaatgaa gcacatagat    420
attgtgctct atcccataac tcagcagcag acatgagtag tgcaagtaat aattttgtct    480
ttctaaaaaa tgaaggatta cttgacatat catttatgct gaacgcatgc tatgacgtag    540
taggcgaagg catacctttt tctccttata tatgcgcagg tatcggtact gatttagtat    600
ccatgtttga agctacaaat cctaaaattt cttaccaagg aaagttaggt ttaagctact    660
ctataagccc agaagcttct gtgtttattg gtgggcactt tcataaggta atagggaacg    720
aatttagaga tattcctact ataataccta ctggatcaac acttgcagga aaaggaaact    780
accctgcaat agtaatactg gatgtatgcc actttggaat agaaatggga               830

<210> SEQ ID NO 12
<211> LENGTH: 864
<212> TYPE: DNA
<213> ORGANISM: Ehrlichia canis

<400> SEQUENCE: 12
atatgaaata taaaaaaact tttacagtaa ctgcattagt attattaact tcctttacac     60
attttatacc tttttatagt ccagcacgtg ccagtacaat tcacaacttc tacattagtg    120
gaaaatatat gccaacagcg tcacattttg gaatttttttc agctaaagaa gaacaaagtt   180
ttactaaggt attagttggg ttagatcaac gattatcaca taatattata aacaataatg    240
atacagcaaa gagtcttaag gttcaaaatt attcatttaa atacaaaaat aacccatttc    300
taggatttgc aggagctatt ggttattcaa taggcaattc aagaatagaa ctagaagtat    360
cacatgaaat atttgatact aaaaacccag gaaacaatta tttaaatgac tctcacaaat    420
attgcgcttt atctcatgga agtcacatat gcagtgatgg aaatagcgga gattggtaca    480
ctgcaaaaac tgataagttt gtacttctga aaaatgaagg tttacttgac gtctcattta    540
tgttaaacgc atgttatgac ataacaactg aaaaaatgcc tttttcacct tatatatgtg    600
caggtattgg tactgatctc atatctatgt ttgagacaac acaaaacaaa atatcttatc    660
aaggaaagtt aggtttaaac tatactataa actcaagagt ttctgttttt gcaggtgggc    720
actttcataa ggtaataggt aatgaattta aaggtattcc tactctatta cctgatggat    780
caaacattaa agtacaacag tctgcaacag taacattaga tgtgtgccat ttcgggttag    840
agattggaag tagatttttc tttt                                           864

<210> SEQ ID NO 13
<211> LENGTH: 399
<212> TYPE: DNA
<213> ORGANISM: Ehrlichia canis
<400> SEQUENCE: 13
atatgaattg taaaaaagtt ttcacaataa gtgcattgat atcatccata tacttcctac     60
```

```
ctaatgtctc atactctaac ccagtatatg gtaacagtat gtatggtaat ttttacatat    120
caggaaagta catgccaagt gttcctcatt ttggaatttt ttcagctgaa gaagagaaaa    180
aaaagacaac tgtagtatat ggcttaaaag aaaactgggc aggagatgca atatctagtc    240
aaagtccaga tgataatttt accattcgaa attactcatt caagtatgca agcaacaagt    300
ttttagggtt tgcagtagct attggttact cgataggcag tccaagaata gaagttgaga    360
tgtcttatga agcatttgat gtaaaaaatc aaggtaaca                           399
```

<210> SEQ ID NO 14
<211> LENGTH: 43
<212> TYPE: PRT
<213> ORGANISM: Ehrlichia chaffeensis

<400> SEQUENCE: 14

```
Asn Glu Phe Arg Asp Ile Ser Thr Leu Lys Ala Phe Ala Thr Pro Ser
  1               5                  10                  15

Ser Ala Ala Thr Pro Asp Leu Ala Thr Val Thr Leu Ser Val Cys His
             20                  25                  30

Phe Gly Val Glu Leu Gly Gly Arg Phe Asn Phe
         35                  40
```

<210> SEQ ID NO 15
<211> LENGTH: 286
<212> TYPE: PRT
<213> ORGANISM: Ehrlichia chaffeensis

<400> SEQUENCE: 15

```
Met Asn Cys Glu Lys Phe Phe Ile Thr Thr Ala Leu Thr Leu Leu Met
  1               5                  10                  15

Ser Phe Leu Pro Gly Ile Ser Leu Ser Asp Pro Val Gln Asp Asp Asn
             20                  25                  30

Ile Ser Gly Asn Phe Tyr Ile Ser Gly Lys Tyr Met Pro Ser Ala Ser
         35                  40                  45

His Phe Gly Val Phe Ser Ala Lys Glu Glu Arg Asn Thr Thr Val Gly
     50                  55                  60

Val Phe Gly Ile Glu Gln Asp Trp Asp Arg Cys Val Ile Ser Arg Thr
 65                  70                  75                  80

Thr Leu Ser Asp Ile Phe Thr Val Pro Asn Tyr Ser Phe Lys Tyr Glu
                 85                  90                  95

Asn Asn Leu Phe Ser Gly Phe Ala Gly Ala Ile Gly Tyr Ser Met Asp
            100                 105                 110

Gly Pro Arg Ile Glu Leu Glu Val Ser Tyr Glu Ala Phe Asp Val Lys
        115                 120                 125

Asn Gln Gly Asn Asn Tyr Lys Asn Glu Ala His Arg Tyr Tyr Ala Leu
    130                 135                 140

Ser His Leu Leu Gly Thr Glu Thr Gln Ile Asp Gly Ala Gly Ser Ala
145                 150                 155                 160

Ser Val Phe Leu Ile Asn Glu Gly Leu Leu Asp Lys Ser Phe Met Leu
                165                 170                 175

Asn Ala Cys Tyr Asp Val Ile Ser Glu Gly Ile Pro Phe Ser Pro Tyr
            180                 185                 190

Ile Cys Ala Gly Ile Gly Ile Asp Leu Val Ser Met Phe Glu Ala Ile
        195                 200                 205

Asn Pro Lys Ile Ser Tyr Gln Gly Lys Leu Gly Leu Ser Tyr Pro Ile
    210                 215                 220

Ser Pro Glu Ala Ser Val Phe Ile Gly Gly His Phe His Lys Val Ile
```

```
225                 230                 235                 240

Gly Asn Glu Phe Arg Asp Ile Pro Thr Met Ile Pro Ser Glu Ser Ala
                245                 250                 255

Leu Ala Gly Lys Gly Asn Tyr Pro Ala Ile Val Thr Leu Asp Val Phe
            260                 265                 270

Tyr Phe Gly Ile Glu Leu Gly Gly Arg Phe Asn Phe Gln Leu
        275                 280                 285

<210> SEQ ID NO 16
<211> LENGTH: 278
<212> TYPE: PRT
<213> ORGANISM: Ehrlichia chaffeensis

<400> SEQUENCE: 16

Met Asn Cys Lys Lys Phe Phe Ile Thr Thr Ala Leu Val Ser Leu Met
 1               5                  10                  15

Ser Phe Leu Pro Gly Ile Ser Phe Ser Asp Pro Val Gln Gly Asp Asn
                20                  25                  30

Ile Ser Gly Asn Phe Tyr Val Ser Gly Lys Tyr Met Pro Ser Ala Ser
            35                  40                  45

His Phe Gly Met Phe Ser Ala Lys Glu Glu Lys Asn Pro Thr Val Ala
        50                  55                  60

Leu Tyr Gly Leu Lys Gln Asp Trp Glu Gly Ile Ser Ser Ser Ser His
65                  70                  75                  80

Asn Asp Asn His Phe Asn Asn Lys Gly Tyr Ser Phe Lys Tyr Glu Asn
                85                  90                  95

Asn Pro Phe Leu Gly Phe Ala Gly Ala Ile Gly Tyr Ser Met Gly Gly
                100                 105                 110

Pro Arg Val Glu Phe Glu Val Ser Tyr Glu Thr Phe Asp Val Lys Asn
        115                 120                 125

Gln Gly Asn Asn Tyr Lys Asn Asp Ala His Arg Tyr Cys Ala Leu Gly
    130                 135                 140

Gln Gln Asp Asn Ser Gly Ile Pro Lys Thr Ser Lys Tyr Val Leu Leu
145                 150                 155                 160

Lys Ser Glu Gly Leu Leu Asp Ile Ser Phe Met Leu Asn Ala Cys Tyr
                165                 170                 175

Asp Ile Ile Asn Glu Ser Ile Pro Leu Ser Pro Tyr Ile Cys Ala Gly
                180                 185                 190

Val Gly Thr Asp Leu Ile Ser Met Phe Glu Ala Thr Asn Pro Lys Ile
        195                 200                 205

Ser Tyr Gln Gly Lys Leu Gly Leu Ser Tyr Ser Ile Asn Pro Glu Ala
    210                 215                 220

Ser Val Phe Ile Gly Gly His Phe His Lys Val Ile Gly Asn Glu Phe
225                 230                 235                 240

Arg Asp Ile Pro Thr Leu Lys Ala Phe Val Thr Ser Ser Ala Thr Pro
                245                 250                 255

Asp Leu Ala Ile Val Thr Leu Ser Val Cys His Phe Gly Ile Glu Leu
                260                 265                 270

Gly Gly Arg Phe Asn Phe
        275

<210> SEQ ID NO 17
<211> LENGTH: 280
<212> TYPE: PRT
<213> ORGANISM: Ehrlichia chaffeensis
```

-continued

<400> SEQUENCE: 17

Met Asn Cys Lys Lys Phe Phe Ile Thr Thr Thr Leu Val Ser Leu Met
 1               5                  10                  15

Ser Phe Leu Pro Gly Ile Ser Phe Ser Asp Ala Val Gln Asn Asp Asn
             20                  25                  30

Val Gly Gly Asn Phe Tyr Ile Ser Gly Lys Tyr Val Pro Ser Val Ser
         35                  40                  45

His Phe Gly Val Phe Ser Ala Lys Gln Glu Arg Asn Thr Thr Ile Gly
     50                  55                  60

Val Phe Gly Leu Lys Gln Asp Trp Asp Gly Ser Thr Ile Ser Lys Asn
 65                  70                  75                  80

Ser Pro Glu Asn Thr Phe Asn Val Pro Asn Tyr Ser Phe Lys Tyr Glu
                 85                  90                  95

Asn Asn Pro Phe Leu Gly Phe Ala Gly Ala Val Gly Tyr Leu Met Asn
            100                 105                 110

Gly Pro Arg Ile Glu Leu Glu Met Ser Tyr Glu Thr Phe Asp Val Lys
        115                 120                 125

Asn Gln Gly Asn Asn Tyr Lys Asn Asp Ala His Lys Tyr Tyr Ala Leu
    130                 135                 140

Thr His Asn Ser Gly Gly Lys Leu Ser Asn Ala Gly Asp Lys Phe Val
145                 150                 155                 160

Phe Leu Lys Asn Glu Gly Leu Leu Asp Ile Ser Leu Met Leu Asn Ala
                165                 170                 175

Cys Tyr Asp Val Ile Ser Glu Gly Ile Pro Phe Ser Pro Tyr Ile Cys
            180                 185                 190

Ala Gly Val Gly Thr Asp Leu Ile Ser Met Phe Glu Ala Ile Asn Pro
        195                 200                 205

Lys Ile Ser Tyr Gln Gly Lys Leu Gly Leu Ser Tyr Ser Ile Ser Pro
    210                 215                 220

Glu Ala Ser Val Phe Val Gly Gly His Phe His Lys Val Ile Gly Asn
225                 230                 235                 240

Glu Phe Arg Asp Ile Pro Ala Met Ile Pro Ser Thr Ser Thr Leu Thr
                245                 250                 255

Gly Asn His Phe Thr Ile Val Thr Leu Ser Val Cys His Phe Gly Val
            260                 265                 270

Glu Leu Gly Gly Arg Phe Asn Phe
        275                 280

<210> SEQ ID NO 18
<211> LENGTH: 276
<212> TYPE: PRT
<213> ORGANISM: Ehrlichia chaffeensis

<400> SEQUENCE: 18

Met Asn Tyr Lys Lys Val Phe Ile Thr Ser Ala Leu Ile Ser Leu Ile
1 5 10 15

Ser Ser Leu Pro Gly Val Ser Phe Ser Asp Pro Ala Gly Ser Gly Ile
20 25 30

Asn Gly Asn Phe Tyr Ile Ser Gly Lys Tyr Met Pro Ser Ala Ser His
35 40 45

Phe Gly Val Phe Ser Ala Lys Glu Glu Arg Asn Thr Thr Val Gly Val
50 55 60

Phe Gly Leu Lys Gln Asn Trp Asp Gly Ser Ala Ile Ser Asn Ser Ser
65 70 75 80

-continued

```
Pro Asn Asp Val Phe Thr Val Ser Asn Tyr Ser Phe Lys Tyr Glu Asn
                85                  90                  95

Asn Pro Phe Leu Gly Phe Ala Gly Ala Ile Gly Tyr Ser Met Asp Gly
            100                 105                 110

Pro Arg Ile Glu Leu Glu Val Ser Tyr Glu Thr Phe Asp Val Lys Asn
        115                 120                 125

Gln Gly Asn Asn Tyr Lys Asn Glu Ala His Arg Tyr Cys Ala Leu Ser
    130                 135                 140

His Asn Ser Ala Ala Asp Met Ser Ser Ala Ser Asn Asn Phe Val Phe
145                 150                 155                 160

Leu Lys Asn Glu Gly Leu Leu Asp Ile Ser Phe Met Leu Asn Ala Cys
                165                 170                 175

Tyr Asp Val Val Gly Glu Gly Ile Pro Phe Ser Pro Tyr Ile Cys Ala
            180                 185                 190

Gly Ile Gly Thr Asp Leu Val Ser Met Phe Glu Ala Thr Asn Pro Lys
        195                 200                 205

Ile Ser Tyr Gln Gly Lys Leu Gly Leu Ser Tyr Ser Ile Ser Pro Glu
    210                 215                 220

Ala Ser Val Phe Ile Gly Gly His Phe His Lys Val Ile Gly Asn Glu
225                 230                 235                 240

Phe Arg Asp Ile Pro Thr Ile Pro Thr Gly Ser Thr Leu Ala Gly
                245                 250                 255

Lys Gly Asn Tyr Pro Ala Ile Val Ile Leu Asp Val Cys His Phe Gly
            260                 265                 270

Ile Glu Met Gly
        275
```

<210> SEQ ID NO 19
<211> LENGTH: 287
<212> TYPE: PRT
<213> ORGANISM: Ehrlichia canis

<400> SEQUENCE: 19

```
Met Lys Tyr Lys Lys Thr Phe Thr Val Thr Ala Leu Val Leu Leu Thr
  1               5                  10                  15

Ser Phe Thr His Phe Ile Pro Phe Tyr Ser Pro Ala Arg Ala Ser Thr
                 20                  25                  30

Ile His Asn Phe Tyr Ile Ser Gly Lys Tyr Met Pro Thr Ala Ser His
             35                  40                  45

Phe Gly Ile Phe Ser Ala Lys Glu Gln Ser Phe Thr Lys Val Leu
     50                  55                  60

Val Gly Leu Asp Gln Arg Leu Ser His Asn Ile Ile Asn Asn Asn Asp
 65                  70                  75                  80

Thr Ala Lys Ser Leu Lys Val Gln Asn Tyr Ser Phe Lys Tyr Lys Asn
                 85                  90                  95

Asn Pro Phe Leu Gly Phe Ala Gly Ala Ile Gly Tyr Ser Ile Gly Asn
            100                 105                 110

Ser Arg Ile Glu Leu Glu Val Ser His Glu Ile Phe Asp Thr Lys Asn
        115                 120                 125

Pro Gly Asn Asn Tyr Leu Asn Asp Ser His Lys Tyr Cys Ala Leu Ser
    130                 135                 140

His Gly Ser His Ile Cys Ser Asp Gly Asn Ser Gly Asp Trp Tyr Thr
145                 150                 155                 160

Ala Lys Thr Asp Lys Phe Val Leu Leu Lys Asn Glu Gly Leu Leu Asp
                165                 170                 175
```

-continued

```
Val Ser Phe Met Leu Asn Ala Cys Tyr Asp Ile Thr Thr Glu Lys Met
            180                 185                 190

Pro Phe Ser Pro Tyr Ile Cys Ala Gly Ile Gly Thr Asp Leu Ile Ser
        195                 200                 205

Met Phe Glu Thr Thr Gln Asn Lys Ile Ser Tyr Gln Gly Lys Leu Gly
    210                 215                 220

Leu Asn Tyr Thr Ile Asn Ser Arg Val Ser Val Phe Ala Gly Gly His
225                 230                 235                 240

Phe His Lys Val Ile Gly Asn Glu Phe Lys Gly Ile Pro Thr Leu Leu
                245                 250                 255

Pro Asp Gly Ser Asn Ile Lys Val Gln Gln Ser Ala Thr Val Thr Leu
            260                 265                 270

Asp Val Cys His Phe Gly Leu Glu Ile Gly Ser Arg Phe Phe Phe
        275                 280                 285

<210> SEQ ID NO 20
<211> LENGTH: 133
<212> TYPE: PRT
<213> ORGANISM: Ehrlichia canis

<400> SEQUENCE: 20

Met Asn Cys Lys Lys Val Phe Thr Ile Ser Ala Leu Ile Ser Ser Ile
  1               5                  10                  15

Tyr Phe Leu Pro Asn Val Ser Tyr Ser Asn Pro Val Tyr Gly Asn Ser
             20                  25                  30

Met Tyr Gly Asn Phe Tyr Ile Ser Gly Lys Tyr Met Pro Ser Val Pro
         35                  40                  45

His Phe Gly Ile Phe Ser Ala Glu Glu Glu Lys Lys Lys Thr Thr Val
     50                  55                  60

Val Tyr Gly Leu Lys Glu Asn Trp Ala Gly Asp Ala Ile Ser Ser Gln
 65                  70                  75                  80

Ser Pro Asp Asp Asn Phe Thr Ile Arg Asn Tyr Ser Phe Lys Tyr Ala
                 85                  90                  95

Ser Asn Lys Phe Leu Gly Phe Ala Val Ala Ile Gly Tyr Ser Ile Gly
            100                 105                 110

Ser Pro Arg Ile Glu Val Glu Met Ser Tyr Glu Ala Phe Asp Val Lys
        115                 120                 125

Asn Gln Gly Asn Asn
    130

<210> SEQ ID NO 21
<211> LENGTH: 686
<212> TYPE: DNA
<213> ORGANISM: Ehrlichia canis

<400> SEQUENCE: 21
atgaaagcta tcaaattcat acttaatgtc tgcttactat ttgcagcaat atttttaggg      60
tattcctata ttacaaaaca aggcatattt caaacaaaac atcatgatac acctaatact     120
actataccaa atgaagacgg tattcaatct agctttagct taatcaatca agacggtaaa     180
acagtaacca gccaagattt cctagggaaa cacatgttag ttttgtttgg attctctgca     240
tgtaaaagca tttgccctgc agaattggga ttagtatctg aagcacttgc acaacttggt     300
aataatgcag acaaattaca agtaattttt attacaattg atccaaaaaa tgatactgta     360
gaaaaattaa aagaatttca tgaacatttt gattcaagaa ttcaaatgtt aacaggaaat     420

-continued

```
actgaagaca ttaatcaaat aattaaaaat tataaaatat atgttggaca agcagataaa    480
gatcatcaaa ttaaccattc tgcaataatg taccttattg acaaaaaagg atcatatctt    540
tcacacttca ttccagattt aaaatcacaa gaaaatcaag tagataagtt actatcttta    600
gttaagcagt atctgtaaat aaattcatgg aatacgttgg atgagtaggt tttttttagt    660 attttttagtg ctaataacat tggcat                                        686
```

<210> SEQ ID NO 22
<211> LENGTH: 618
<212> TYPE: DNA
<213> ORGANISM: Ehrlichia chaffeensis

<400> SEQUENCE: 22

```
atgaaagtta tcaaatttat acttaatatc tgtttattat ttgcagcaat ttttctagga     60
tattcctacg taacaaaaca aggcattttt caagtaagag atcataacac tcccaataca    120
aatatatcaa ataaagccag cattactact agtttttcgt tagtaaatca agatggaaat    180
acagtaaata gtcaagattt tttgggaaaa tacatgctag ttttatttgg attttcttca    240
tgtaaaagca tctgccctgc tgaattagga atagcatctg aagttctctc acagcttggt    300
aatgacacag acaagttaca agtaattttc attacaattg atccaacaaa tgatactgta    360
caaaaattaa aaacatttca tgaacatttt gatcctagaa ttcaaatgct aacaggcagt    420
gcagaagata ttgaaaaaat aataaaaaat tacaaaatat atgttggaca agcagataaa    480
gataatcaaa ttgatcactc tgccataatg tacattatcg ataaaaaagg agaatacatt    540
tcacactttt ctccagattt aaaatcaaca gaaaatcaag tagataagtt actatctata    600
ataaaacaat atctctaa                                                   618
```

<210> SEQ ID NO 23
<211> LENGTH: 205
<212> TYPE: PRT
<213> ORGANISM: Ehrlichia canis

<400> SEQUENCE: 23

```
Met Lys Ala Ile Lys Phe Ile Leu Asn Val Cys Leu Leu Phe Ala Ala
  1               5                  10                  15

Ile Phe Leu Gly Tyr Ser Tyr Ile Thr Lys Gln Gly Ile Phe Gln Thr
             20                  25                  30

Lys His His Asp Thr Pro Asn Thr Thr Ile Pro Asn Glu Asp Gly Ile
         35                  40                  45

Gln Ser Ser Phe Ser Leu Ile Asn Gln Asp Gly Lys Thr Val Thr Ser
     50                  55                  60

Gln Asp Phe Leu Gly Lys His Met Leu Val Leu Phe Gly Phe Ser Ala
 65                  70                  75                  80

Cys Lys Ser Ile Cys Pro Ala Glu Leu Gly Leu Val Ser Glu Ala Leu
                 85                  90                  95

Ala Gln Leu Gly Asn Asn Ala Asp Lys Leu Gln Val Ile Phe Ile Thr
            100                 105                 110

Ile Asp Pro Lys Asn Asp Thr Val Glu Lys Leu Lys Glu Phe His Glu
        115                 120                 125

His Phe Asp Ser Arg Ile Gln Met Leu Thr Gly Asn Thr Glu Asp Ile
    130                 135                 140

Asn Gln Ile Ile Lys Asn Tyr Lys Ile Tyr Val Gly Gln Ala Asp Lys
145                 150                 155                 160

Asp His Gln Ile Asn His Ser Ala Ile Met Tyr Leu Ile Asp Lys Lys
                165                 170                 175
```

-continued

```
Gly Ser Tyr Leu Ser His Phe Ile Pro Asp Leu Lys Ser Gln Glu Asn
            180                 185                 190

Gln Val Asp Lys Leu Leu Ser Leu Val Lys Gln Tyr Leu
        195                 200                 205

<210> SEQ ID NO 24
<211> LENGTH: 205
<212> TYPE: PRT
<213> ORGANISM: Ehrlichia chaffeensis

<400> SEQUENCE: 24

Met Lys Val Ile Lys Phe Ile Leu Asn Ile Cys Leu Leu Phe Ala Ala
  1               5                  10                  15

Ile Phe Leu Gly Tyr Ser Tyr Val Thr Lys Gln Gly Ile Phe Gln Val
             20                  25                  30

Arg Asp His Asn Thr Pro Asn Thr Asn Ile Ser Asn Lys Ala Ser Ile
         35                  40                  45

Thr Thr Ser Phe Ser Leu Val Asn Gln Asp Gly Asn Thr Val Asn Ser
     50                  55                  60

Gln Asp Phe Leu Gly Lys Tyr Met Leu Val Leu Phe Gly Phe Ser Ser
 65                  70                  75                  80

Cys Lys Ser Ile Cys Pro Ala Glu Leu Gly Ile Ala Ser Glu Val Leu
                 85                  90                  95

Ser Gln Leu Gly Asn Asp Thr Asp Lys Leu Gln Val Ile Phe Ile Thr
            100                 105                 110

Ile Asp Pro Thr Asn Asp Thr Val Gln Lys Leu Lys Thr Phe His Glu
        115                 120                 125

His Phe Asp Pro Arg Ile Gln Met Leu Thr Gly Ser Ala Glu Asp Ile
    130                 135                 140

Glu Lys Ile Ile Lys Asn Tyr Lys Ile Tyr Val Gly Gln Ala Asp Lys
145                 150                 155                 160

Asp Asn Gln Ile Asp His Ser Ala Ile Met Tyr Ile Ile Asp Lys Lys
                165                 170                 175

Gly Glu Tyr Ile Ser His Phe Ser Pro Asp Leu Lys Ser Thr Glu Asn
            180                 185                 190

Gln Val Asp Lys Leu Leu Ser Ile Ile Lys Gln Tyr Leu
        195                 200                 205

<210> SEQ ID NO 25
<211> LENGTH: 618
<212> TYPE: DNA
<213> ORGANISM: Cowdria ruminantium
<220> FEATURE:
<221> NAME/KEY: CDS
<222> LOCATION: (1)..(615)

<400> SEQUENCE: 25 atg aag gct atc aag ttt ata ctt aat cta tgt tta cta ttt gca gca       48
Met Lys Ala Ile Lys Phe Ile Leu Asn Leu Cys Leu Leu Phe Ala Ala
  1               5                  10                  15 att ttt ttg gga tat tct tac ata aca aaa caa ggt ata ttc caa cca       96
Ile Phe Leu Gly Tyr Ser Tyr Ile Thr Lys Gln Gly Ile Phe Gln Pro
             20                  25                  30 aaa tta cac gac tct cct gat gtt aat ata tcg aac aaa gcg gat ata      144
Lys Leu His Asp Ser Pro Asp Val Asn Ile Ser Asn Lys Ala Asp Ile
         35                  40                  45 aat act agc ttt agc tta att aat cag gat ggt att acg ata tct agt      192
Asn Thr Ser Phe Ser Leu Ile Asn Gln Asp Gly Ile Thr Ile Ser Ser
```

```
aaa gac ttc ctt gga aaa cat atg tta gtc ctt ttt ggg ttt tct tct     240
Lys Asp Phe Leu Gly Lys His Met Leu Val Leu Phe Gly Phe Ser Ser
 65              70                  75                  80 tgt aaa act att tgc ccc atg gaa cta ggg tta gca tcc aca att cta     288
Cys Lys Thr Ile Cys Pro Met Glu Leu Gly Leu Ala Ser Thr Ile Leu
                 85                  90                  95 gat caa ctt ggc aac gaa tct gac aag tta caa gta gtc ttt ata act     336
Asp Gln Leu Gly Asn Glu Ser Asp Lys Leu Gln Val Val Phe Ile Thr
            100                 105                 110 att gat cca aca aaa gat act gta gaa aca cta aaa gag ttt cac aaa     384
Ile Asp Pro Thr Lys Asp Thr Val Glu Thr Leu Lys Glu Phe His Lys
        115                 120                 125 aat ttt gac tca cgg att caa atg tta aca gga aac att gaa gct att     432
Asn Phe Asp Ser Arg Ile Gln Met Leu Thr Gly Asn Ile Glu Ala Ile
    130                 135                 140 aat caa ata gta caa ggg tac aaa gta tat gta ggt cag cca gac aat     480
Asn Gln Ile Val Gln Gly Tyr Lys Val Tyr Val Gly Gln Pro Asp Asn
145                 150                 155                 160 gat aac caa att aac cat tct gga ata atg tat att gta gac aag aaa     528
Asp Asn Gln Ile Asn His Ser Gly Ile Met Tyr Ile Val Asp Lys Lys
                165                 170                 175 gga gaa tat tta aca cat ttt gta cca gat tta aag tca aaa gag cct     576
Gly Glu Tyr Leu Thr His Phe Val Pro Asp Leu Lys Ser Lys Glu Pro
            180                 185                 190 caa gtg gat aaa tta ctt tct tta att aag cag tat ctt taa             618
Gln Val Asp Lys Leu Leu Ser Leu Ile Lys Gln Tyr Leu
        195                 200                 205
```

<210> SEQ ID NO 26
<211> LENGTH: 205
<212> TYPE: PRT
<213> ORGANISM: Cowdria ruminantium

<400> SEQUENCE: 26

```
Met Lys Ala Ile Lys Phe Ile Leu Asn Leu Cys Leu Leu Phe Ala Ala
 1                5                  10                  15

Ile Phe Leu Gly Tyr Ser Tyr Ile Thr Lys Gln Gly Ile Phe Gln Pro
             20                  25                  30

Lys Leu His Asp Ser Pro Asp Val Asn Ile Ser Asn Lys Ala Asp Ile
         35                  40                  45

Asn Thr Ser Phe Ser Leu Ile Asn Gln Asp Gly Ile Thr Ile Ser Ser
     50                  55                  60

Lys Asp Phe Leu Gly Lys His Met Leu Val Leu Phe Gly Phe Ser Ser
 65                  70                  75                  80

Cys Lys Thr Ile Cys Pro Met Glu Leu Gly Leu Ala Ser Thr Ile Leu
                 85                  90                  95

Asp Gln Leu Gly Asn Glu Ser Asp Lys Leu Gln Val Val Phe Ile Thr
            100                 105                 110

Ile Asp Pro Thr Lys Asp Thr Val Glu Thr Leu Lys Glu Phe His Lys
        115                 120                 125

Asn Phe Asp Ser Arg Ile Gln Met Leu Thr Gly Asn Ile Glu Ala Ile
    130                 135                 140

Asn Gln Ile Val Gln Gly Tyr Lys Val Tyr Val Gly Gln Pro Asp Asn
145                 150                 155                 160

Asp Asn Gln Ile Asn His Ser Gly Ile Met Tyr Ile Val Asp Lys Lys
                165                 170                 175
```

-continued

```
Gly Glu Tyr Leu Thr His Phe Val Pro Asp Leu Lys Ser Lys Glu Pro
            180                 185                 190

Gln Val Asp Lys Leu Leu Ser Leu Ile Lys Gln Tyr Leu
            195                 200                 205

<210> SEQ ID NO 27
<211> LENGTH: 981
<212> TYPE: DNA
<213> ORGANISM: Cowdria ruminantium
<220> FEATURE:
<221> NAME/KEY: CDS
<222> LOCATION: (1)..(978)

<400> SEQUENCE: 27 atg aag aaa ata ttg gtt acg ttt tta gtt gtt gtt aat gtg ttt tgt       48
Met Lys Lys Ile Leu Val Thr Phe Leu Val Val Val Asn Val Phe Cys
 1               5                  10                  15 aat gct gcc att gct tca act gac tca tca gaa gat aaa cag tat att      96
Asn Ala Ala Ile Ala Ser Thr Asp Ser Ser Glu Asp Lys Gln Tyr Ile
                20                  25                  30 tta att ggt act ggt tct atg act gga gta tat tat cct ata gga ggt     144
Leu Ile Gly Thr Gly Ser Met Thr Gly Val Tyr Tyr Pro Ile Gly Gly
            35                  40                  45 agc ata tgt agg ttt att gca tct gat tat ggt aat gat aat aac agc     192
Ser Ile Cys Arg Phe Ile Ala Ser Asp Tyr Gly Asn Asp Asn Asn Ser
 50                  55                  60 ata gtt tgt tct ata tct tct aca act ggt agc gta tat aat ctt aat     240
Ile Val Cys Ser Ile Ser Ser Thr Thr Gly Ser Val Tyr Asn Leu Asn
 65                  70                  75                  80 tct atg cgt tat gca aat atg gat ata ggt att att caa tct gat tta     288
Ser Met Arg Tyr Ala Asn Met Asp Ile Gly Ile Ile Gln Ser Asp Leu
                 85                  90                  95 gag tac tat gca tat aat ggt att ggt tta tat gaa aaa atg cca gca     336
Glu Tyr Tyr Ala Tyr Asn Gly Ile Gly Leu Tyr Glu Lys Met Pro Ala
            100                 105                 110 atg agg cat cta aga ata tta tct tca tta cat aaa gaa tat ctt aca     384
Met Arg His Leu Arg Ile Leu Ser Ser Leu His Lys Glu Tyr Leu Thr
        115                 120                 125 att gtt gtt agg gcg aat tct aat ata tca gtt att gat gat ata aaa     432
Ile Val Val Arg Ala Asn Ser Asn Ile Ser Val Ile Asp Asp Ile Lys
    130                 135                 140 ggc aaa aga gtt aat att ggt agt cct ggt act ggt gta aga ata gca     480
Gly Lys Arg Val Asn Ile Gly Ser Pro Gly Thr Gly Val Arg Ile Ala
145                 150                 155                 160 atg tta aaa ttg tta aat gaa aaa gga tgg gga aga aaa gat ttt gct     528
Met Leu Lys Leu Leu Asn Glu Lys Gly Trp Gly Arg Lys Asp Phe Ala
                165                 170                 175 gtt atg gca gaa tta aaa tca tca gag caa gct caa gca tta tgt gat     576
Val Met Ala Glu Leu Lys Ser Ser Glu Gln Ala Gln Ala Leu Cys Asp
            180                 185                 190 aat aaa att gat gtg atg gta gat gtt gtt gga cat cct aat gct gca     624
Asn Lys Ile Asp Val Met Val Asp Val Val Gly His Pro Asn Ala Ala
        195                 200                 205 att caa gaa gca gca gca act tgt gat ata aaa ttt att tct tta gat     672
Ile Gln Glu Ala Ala Ala Thr Cys Asp Ile Lys Phe Ile Ser Leu Asp
    210                 215                 220 gat gat ctc ata gat aaa tta cat act aag tat ccc tat tat aaa agg     720
Asp Asp Leu Ile Asp Lys Leu His Thr Lys Tyr Pro Tyr Tyr Lys Arg
225                 230                 235                 240 gat att att agt ggt gcg tta tac agt aac tta cct gat ata caa act     768
Asp Ile Ile Ser Gly Ala Leu Tyr Ser Asn Leu Pro Asp Ile Gln Thr
```

```
                     245                 250                 255
gtt tca gta aaa gct tct tta ata aca act act gaa tta agc aat gag    816
Val Ser Val Lys Ala Ser Leu Ile Thr Thr Thr Glu Leu Ser Asn Glu
            260                 265                 270 ttg gcc tat aaa gtt gtt aaa tct ttg gtt agc cat tta cat gaa cta    864
Leu Ala Tyr Lys Val Val Lys Ser Leu Val Ser His Leu His Glu Leu
            275                 280                 285 cat gga att act gga gct ctt aga aat ctt act gta aaa gac atg gta    912
His Gly Ile Thr Gly Ala Leu Arg Asn Leu Thr Val Lys Asp Met Val
            290                 295                 300 cag tca gat att aca cct tta cat gac ggt gca aaa cgt tat tat aag    960
Gln Ser Asp Ile Thr Pro Leu His Asp Gly Ala Lys Arg Tyr Tyr Lys
305                 310                 315                 320 gaa att gga gtt ata aaa taa                                        981
Glu Ile Gly Val Ile Lys
            325
```

<210> SEQ ID NO 28
<211> LENGTH: 326
<212> TYPE: PRT
<213> ORGANISM: Cowdria ruminantium

<400> SEQUENCE: 28

```
Met Lys Lys Ile Leu Val Thr Phe Leu Val Val Asn Val Phe Cys
 1               5                  10                  15

Asn Ala Ala Ile Ala Ser Thr Asp Ser Ser Glu Asp Lys Gln Tyr Ile
                20                  25                  30

Leu Ile Gly Thr Gly Ser Met Thr Gly Val Tyr Tyr Pro Ile Gly Gly
            35                  40                  45

Ser Ile Cys Arg Phe Ile Ala Ser Asp Tyr Gly Asn Asp Asn Ser
         50                  55                  60

Ile Val Cys Ser Ile Ser Ser Thr Thr Gly Ser Val Tyr Asn Leu Asn
 65                  70                  75                  80

Ser Met Arg Tyr Ala Asn Met Asp Ile Gly Ile Gln Ser Asp Leu
                85                  90                  95

Glu Tyr Tyr Ala Tyr Asn Gly Ile Gly Leu Tyr Glu Lys Met Pro Ala
            100                 105                 110

Met Arg His Leu Arg Ile Leu Ser Ser Leu His Lys Glu Tyr Leu Thr
            115                 120                 125

Ile Val Val Arg Ala Asn Ser Asn Ile Ser Val Ile Asp Asp Ile Lys
        130                 135                 140

Gly Lys Arg Val Asn Ile Gly Ser Pro Gly Thr Gly Val Arg Ile Ala
145                 150                 155                 160

Met Leu Lys Leu Leu Asn Glu Lys Gly Trp Gly Arg Lys Asp Phe Ala
                165                 170                 175

Val Met Ala Glu Leu Lys Ser Ser Glu Gln Ala Gln Ala Leu Cys Asp
            180                 185                 190

Asn Lys Ile Asp Val Met Val Asp Val Val Gly His Pro Asn Ala Ala
        195                 200                 205

Ile Gln Glu Ala Ala Ala Thr Cys Asp Ile Lys Phe Ile Ser Leu Asp
    210                 215                 220

Asp Asp Leu Ile Asp Lys Leu His Thr Tyr Pro Tyr Tyr Lys Arg
225                 230                 235                 240

Asp Ile Ile Ser Gly Ala Leu Tyr Ser Asn Leu Pro Asp Ile Gln Thr
                245                 250                 255

Val Ser Val Lys Ala Ser Leu Ile Thr Thr Thr Glu Leu Ser Asn Glu
```

```
                        260                     265                      270
Leu Ala Tyr Lys Val Lys Ser Leu Val Ser His Leu His Glu Leu
            275                     280                     285
His Gly Ile Thr Gly Ala Leu Arg Asn Leu Thr Val Lys Asp Met Val
            290                     295                     300
Gln Ser Asp Ile Thr Pro Leu His Asp Gly Ala Lys Arg Tyr Tyr Lys
305                     310                     315                     320
Glu Ile Gly Val Ile Lys
                325

<210> SEQ ID NO 29
<211> LENGTH: 519
<212> TYPE: DNA
<213> ORGANISM: Cowdria ruminantium
<220> FEATURE:
<221> NAME/KEY: CDS
<222> LOCATION: (1)..(516)

<400> SEQUENCE: 29 atg aat ata ttc aat tat atg cag ata atg cct aat ata agt gtt gat        48
Met Asn Ile Phe Asn Tyr Met Gln Ile Met Pro Asn Ile Ser Val Asp
 1               5                  10                  15 gca ttt gtt gca cct act gct gta att ata ggt gat gtt tgt gta aat        96
Ala Phe Val Ala Pro Thr Ala Val Ile Ile Gly Asp Val Cys Val Asn
             20                  25                  30 gac aag tgt agc att tgg tat aac tca gta tta cgt gga gat gta ggc       144
Asp Lys Cys Ser Ile Trp Tyr Asn Ser Val Leu Arg Gly Asp Val Gly
         35                  40                  45 caa att gtt att ggt gta ggt act aat att caa gat ggg aca ata ata       192
Gln Ile Val Ile Gly Val Gly Thr Asn Ile Gln Asp Gly Thr Ile Ile
     50                  55                  60 cat gtt gat agg aaa tat ggt aat acg aat att ggc aaa aag gtt act       240
His Val Asp Arg Lys Tyr Gly Asn Thr Asn Ile Gly Lys Lys Val Thr
 65                  70                  75                  80 att ggg cat ggg tgt ata tta cat gct tgt gag ata caa gat tat gtg       288
Ile Gly His Gly Cys Ile Leu His Ala Cys Glu Ile Gln Asp Tyr Val
                 85                  90                  95 ctt gtt gga atg gga tct att att atg gat aac gtt gtg gtt gaa aag       336
Leu Val Gly Met Gly Ser Ile Ile Met Asp Asn Val Val Val Glu Lys
            100                 105                 110 aat gca atg gtg gct gct gga tca tta gtg gta aga ggt aaa gtt gtg       384
Asn Ala Met Val Ala Ala Gly Ser Leu Val Val Arg Gly Lys Val Val
        115                 120                 125 aaa act ggt gaa tta tgg gct ggt agg cct gca caa ttt tta aga atg       432
Lys Thr Gly Glu Leu Trp Ala Gly Arg Pro Ala Gln Phe Leu Arg Met
    130                 135                 140 ttg tct agt gat gaa att aaa gag ata agt aaa tct gct gat aac tat       480
Leu Ser Ser Asp Glu Ile Lys Glu Ile Ser Lys Ser Ala Asp Asn Tyr
145                 150                 155                 160 ata gag ctt gcc agt gat tac ata act ggt aag ttg taa                   519
Ile Glu Leu Ala Ser Asp Tyr Ile Thr Gly Lys Leu
                165                 170

<210> SEQ ID NO 30
<211> LENGTH: 172
<212> TYPE: PRT
<213> ORGANISM: Cowdria ruminantium

<400> SEQUENCE: 30

Met Asn Ile Phe Asn Tyr Met Gln Ile Met Pro Asn Ile Ser Val Asp
 1               5                  10                  15
```

```
Ala Phe Val Ala Pro Thr Ala Val Ile Ile Gly Asp Val Cys Val Asn
            20                  25                  30

Asp Lys Cys Ser Ile Trp Tyr Asn Ser Val Leu Arg Gly Asp Val Gly
        35                  40                  45

Gln Ile Val Ile Gly Val Gly Thr Asn Ile Gln Asp Gly Thr Ile Ile
    50                  55                  60

His Val Asp Arg Lys Tyr Gly Asn Thr Asn Ile Gly Lys Lys Val Thr
65                  70                  75                  80

Ile Gly His Gly Cys Ile Leu His Ala Cys Glu Ile Gln Asp Tyr Val
                85                  90                  95

Leu Val Gly Met Gly Ser Ile Ile Met Asp Asn Val Val Glu Lys
            100                 105                 110

Asn Ala Met Val Ala Ala Gly Ser Leu Val Val Arg Gly Lys Val Val
            115                 120                 125

Lys Thr Gly Glu Leu Trp Ala Gly Arg Pro Ala Gln Phe Leu Arg Met
        130                 135                 140

Leu Ser Ser Asp Glu Ile Lys Glu Ile Ser Lys Ser Ala Asp Asn Tyr
145                 150                 155                 160

Ile Glu Leu Ala Ser Asp Tyr Ile Thr Gly Lys Leu
                165                 170

<210> SEQ ID NO 31
<211> LENGTH: 753
<212> TYPE: DNA
<213> ORGANISM: Cowdria ruminantium
<220> FEATURE:
<221> NAME/KEY: CDS
<222> LOCATION: (1)..(750)

<400> SEQUENCE: 31 atg atg ata aga atc ttt ctt ttg tta ggc tta gta tta tta gta gca      48
Met Met Ile Arg Ile Phe Leu Leu Leu Gly Leu Val Leu Leu Val Ala
 1               5                  10                  15 agt ttt cca cta tta aat aac tgg cta tct aat cat tct ggt aag tct     96
Ser Phe Pro Leu Leu Asn Asn Trp Leu Ser Asn His Ser Gly Lys Ser
            20                  25                  30 act aca ttg gat aag gat gca gtt ata tct ata gtt gag gaa tat ata    144
Thr Thr Leu Asp Lys Asp Ala Val Ile Ser Ile Val Glu Glu Tyr Ile
        35                  40                  45 acc aat tat cct cag agg gta ata gat tta ctt act aca ggc caa gca    192
Thr Asn Tyr Pro Gln Arg Val Ile Asp Leu Leu Thr Thr Gly Gln Ala
    50                  55                  60 caa gca gaa aga gca gag ctt act gaa aat att aaa aaa tat aaa tct    240
Gln Ala Glu Arg Ala Glu Leu Thr Glu Asn Ile Lys Lys Tyr Lys Ser
65                  70                  75                  80 gag ctt gaa gat att gca tac cca tct gct ggc aat aaa gac agt aaa    288
Glu Leu Glu Asp Ile Ala Tyr Pro Ser Ala Gly Asn Lys Asp Ser Lys
                85                  90                  95 att gca ttt att gag ttc ttc gat tac tct tgt ggt tat tgt aaa atg    336
Ile Ala Phe Ile Glu Phe Phe Asp Tyr Ser Cys Gly Tyr Cys Lys Met
            100                 105                 110 atg ttt gaa gat atc aaa caa att ata aaa gat ggt aag gta cgt gtt    384
Met Phe Glu Asp Ile Lys Gln Ile Ile Lys Asp Gly Lys Val Arg Val
            115                 120                 125 att ttt aga gat ttt cca ata ctt ggg gaa tcg tcg tta aag gct gtt    432
Ile Phe Arg Asp Phe Pro Ile Leu Gly Glu Ser Ser Leu Lys Ala Val
        130                 135                 140 aaa gca gca ttg gct gta cat ctt atc aat cca agt aaa tac ttg gac    480
```

```
Lys Ala Ala Leu Ala Val His Leu Ile Asn Pro Ser Lys Tyr Leu Asp
145                 150                 155                 160 ttc tat tat gca gca tta aat cat aaa cag cca ttt aat gat gaa tct      528
Phe Tyr Tyr Ala Ala Leu Asn His Lys Gln Pro Phe Asn Asp Glu Ser
                165                 170                 175 ata ctt aat ata gtt aaa tca ctt gaa att tca gaa gag gaa ttt aaa      576
Ile Leu Asn Ile Val Lys Ser Leu Glu Ile Ser Glu Glu Glu Phe Lys
            180                 185                 190 gat tct tta tct aaa aat tct agt act att gat aag atg ata gag tcc      624
Asp Ser Leu Ser Lys Asn Ser Ser Thr Ile Asp Lys Met Ile Glu Ser
        195                 200                 205 act aga aat ctg gct gag aag tta aat atc aga ggt act cct gct ctt      672
Thr Arg Asn Leu Ala Glu Lys Leu Asn Ile Arg Gly Thr Pro Ala Leu
    210                 215                 220 ata ata ggt gat gca ttc att ggg gga gct gca gat tta tca act tta      720
Ile Ile Gly Asp Ala Phe Ile Gly Gly Ala Ala Asp Leu Ser Thr Leu
225                 230                 235                 240 aga agt aaa ata gta gaa cag cag gaa caa taa                          753
Arg Ser Lys Ile Val Glu Gln Gln Glu Gln
                245                 250

<210> SEQ ID NO 32
<211> LENGTH: 250
<212> TYPE: PRT
<213> ORGANISM: Cowdria ruminantium

<400> SEQUENCE: 32

Met Met Ile Arg Ile Phe Leu Leu Leu Gly Leu Val Leu Leu Val Ala
1               5                   10                  15

Ser Phe Pro Leu Leu Asn Asn Trp Leu Ser Asn His Ser Gly Lys Ser
                20                  25                  30

Thr Thr Leu Asp Lys Asp Ala Val Ile Ser Ile Val Glu Glu Tyr Ile
            35                  40                  45

Thr Asn Tyr Pro Gln Arg Val Ile Asp Leu Leu Thr Thr Gly Gln Ala
        50                  55                  60

Gln Ala Glu Arg Ala Glu Leu Thr Glu Asn Ile Lys Lys Tyr Lys Ser
65                  70                  75                  80

Glu Leu Glu Asp Ile Ala Tyr Pro Ser Ala Gly Asn Lys Asp Ser Lys
                85                  90                  95

Ile Ala Phe Ile Glu Phe Phe Asp Tyr Ser Cys Gly Tyr Cys Lys Met
            100                 105                 110

Met Phe Glu Asp Ile Lys Gln Ile Ile Lys Asp Gly Lys Val Arg Val
        115                 120                 125

Ile Phe Arg Asp Phe Pro Ile Leu Gly Glu Ser Ser Leu Lys Ala Val
    130                 135                 140

Lys Ala Ala Leu Ala Val His Leu Ile Asn Pro Ser Lys Tyr Leu Asp
145                 150                 155                 160

Phe Tyr Tyr Ala Ala Leu Asn His Lys Gln Pro Phe Asn Asp Glu Ser
                165                 170                 175

Ile Leu Asn Ile Val Lys Ser Leu Glu Ile Ser Glu Glu Glu Phe Lys
            180                 185                 190

Asp Ser Leu Ser Lys Asn Ser Ser Thr Ile Asp Lys Met Ile Glu Ser
        195                 200                 205

Thr Arg Asn Leu Ala Glu Lys Leu Asn Ile Arg Gly Thr Pro Ala Leu
    210                 215                 220

Ile Ile Gly Asp Ala Phe Ile Gly Gly Ala Ala Asp Leu Ser Thr Leu
225                 230                 235                 240
```

```
Arg Ser Lys Ile Val Glu Gln Gln Glu Gln
                245                 250

<210> SEQ ID NO 33
<211> LENGTH: 450
<212> TYPE: DNA
<213> ORGANISM: Cowdria ruminantium
<220> FEATURE:
<221> NAME/KEY: CDS
<222> LOCATION: (1)..(447)

<400> SEQUENCE: 33 atg cat aga tca aat att att gaa att ttt ata gga ttc cta gtg tta      48
Met His Arg Ser Asn Ile Ile Glu Ile Phe Ile Gly Phe Leu Val Leu
 1               5                  10                  15 gca gga gca ata tct att ggg ata ata gca ttt aac aaa tta cca tat      96
Ala Gly Ala Ile Ser Ile Gly Ile Ile Ala Phe Asn Lys Leu Pro Tyr
             20                  25                  30 aaa aat acc ttg cgt aat tgt tat aca gtt aaa gca ttt ttc tca aat     144
Lys Asn Thr Leu Arg Asn Cys Tyr Thr Val Lys Ala Phe Phe Ser Asn
         35                  40                  45 gta gat ggg ttg gac ata gga gat gaa gta aca ata tca gga gta aaa     192
Val Asp Gly Leu Asp Ile Gly Asp Glu Val Thr Ile Ser Gly Val Lys
     50                  55                  60 ata ggt aca gta act tca ata tca ttg aat gaa agc tat act cct ata     240
Ile Gly Thr Val Thr Ser Ile Ser Leu Asn Glu Ser Tyr Thr Pro Ile
 65                  70                  75                  80 gta aca atg tgc ata cag aaa aat atc tta cta cct tca gat agt tca     288
Val Thr Met Cys Ile Gln Lys Asn Ile Leu Leu Pro Ser Asp Ser Ser
                 85                  90                  95 gca tct ata tta aac agc aat atg tta gga aaa aag cac att gat atc     336
Ala Ser Ile Leu Asn Ser Asn Met Leu Gly Lys Lys His Ile Asp Ile
            100                 105                 110 gaa ctt gga tca gat caa gaa gtc atc gta agt gaa ggt tta ata gaa     384
Glu Leu Gly Ser Asp Gln Glu Val Ile Val Ser Glu Gly Leu Ile Glu
        115                 120                 125 cat aca cat tca gat tta agt ttc aat gca att att gct aaa ata ata     432
His Thr His Ser Asp Leu Ser Phe Asn Ala Ile Ile Ala Lys Ile Ile
    130                 135                 140 gat tca ctt att aag tag                                             450
Asp Ser Leu Ile Lys
145

<210> SEQ ID NO 34
<211> LENGTH: 149
<212> TYPE: PRT
<213> ORGANISM: Cowdria ruminantium

<400> SEQUENCE: 34

Met His Arg Ser Asn Ile Ile Glu Ile Phe Ile Gly Phe Leu Val Leu
 1               5                  10                  15

Ala Gly Ala Ile Ser Ile Gly Ile Ile Ala Phe Asn Lys Leu Pro Tyr
             20                  25                  30

Lys Asn Thr Leu Arg Asn Cys Tyr Thr Val Lys Ala Phe Phe Ser Asn
         35                  40                  45

Val Asp Gly Leu Asp Ile Gly Asp Glu Val Thr Ile Ser Gly Val Lys
     50                  55                  60

Ile Gly Thr Val Thr Ser Ile Ser Leu Asn Glu Ser Tyr Thr Pro Ile
 65                  70                  75                  80

Val Thr Met Cys Ile Gln Lys Asn Ile Leu Leu Pro Ser Asp Ser Ser
```

-continued

```
                    85                  90                  95
Ala Ser Ile Leu Asn Ser Asn Met Leu Gly Lys Lys His Ile Asp Ile
                100                 105                 110
Glu Leu Gly Ser Asp Gln Glu Val Ile Val Ser Glu Gly Leu Ile Glu
            115                 120                 125
His Thr His Ser Asp Leu Ser Phe Asn Ala Ile Ile Ala Lys Ile Ile
        130                 135                 140
Asp Ser Leu Ile Lys
145
```

What is claimed is:

1. A method for detecting, in a human or an animal, antibodies having serologic reactivity with the polypeptide of SEQ ID NO:19 comprising the steps of:
 a) contacting a composition containing a carrier and an isolated polypeptide variant of SEQ ID NO:19 with a biological fluid from an animal or human; and
 b) detecting the formation of polypeptide-antibody complexes;
  wherein said isolated polypeptide variant is serologically reactive with antibodies, found in biological fluids of animals or humans, that bind to SEQ ID NO:19 and wherein said isolated polypeptide variant; a) is a fragment of SEQ ID NO:19; b) comprises SEQ ID NO:19 and additional amino acids; c) is a polypeptide variant of SEQ ID NO:19 that has amino acid deletions; or d) is a polypeptide sequence that contains amino acid substitutions within the sequence of SEQ ID NO:19.

2. The method according to claim 1, wherein said isolated polypeptide variant of SEQ ID NO:19 is a fragment of SEQ ID NO:19.

3. The method according to claim 1, wherein said isolated polypeptide variant of SEQ ID NO:19 comprises additional amino acids.

4. The method according to claim 1, wherein said isolated polypeptide variant of SEQ ID NO:19 is a polypeptide variant of SEQ ID NO:19 that has amino acid deletions.

5. A method for detecting, in a human or an animal, antibodies having serologic reactivity with the polypeptide of SEQ ID NO:19 comprising the steps of:
 a) contacting a composition containing a carrier and an isolated polypeptide comprising the sequence of SEQ ID NO:19 with a biological fluid from an animal or human; and
 b) detecting the formation of polypeptide-antibody complexes.

6. A method for detecting, in a human or an animal, antibodies having serologic reactivity with the polypeptide of SEQ ID NO:19 comprising the steps of:
 a) contacting a composition containing a carrier and isolated polypeptide fragments of SEQ ID NO:19 with a biological fluid from an animal or human; and
 b) detecting the formation of polypeptide-antibody complexes;
  wherein said polypeptide fragments are serologically recognized by antibodies, found in biological fluids of an animal or human, that bind to the polypeptide of SEQ ID NO:19.

* * * * *

UNITED STATES PATENT AND TRADEMARK OFFICE
CERTIFICATE OF CORRECTION

PATENT NO.     : 6,593,147 B1                                                              Page 1 of 1
DATED          : July 15, 2003
INVENTOR(S)    : Anthony F. Barbet et al.

It is certified that error appears in the above-identified patent and that said Letters Patent is hereby corrected as shown below:

<u>Column 1,</u>
Line 1, "Nucleic Acid Vaccines Against Rickettsial Diseases and Methods of Use" should read -- Method of Detecting Infection by Ehrlichia by Detection of Antibodies in a Biological Fluid --.

<u>Column 2,</u>
Line 64, "R. rickettsi" should read -- R. rickettsii --.

<u>Column 9,</u>
Line 6, "wash,-" should read -- wash) ; --.
Line 15, "0.2xor" should read -- 0.2x or --.

Signed and Sealed this

Thirtieth Day of December, 2003

JAMES E. ROGAN
*Director of the United States Patent and Trademark Office*